US011160764B2

(12) United States Patent
Haddleton et al.

(10) Patent No.: US 11,160,764 B2
(45) Date of Patent: Nov. 2, 2021

(54) DRUG DELIVERY COMPOSITION CONTAINING SILYL POLYMERS

(71) Applicants: Medherant Limited, Coventry (GB); Bostik SA, Colombes (FR)

(72) Inventors: David Haddleton, Coventry (GB); David Goubard, Compiegne (FR); Ciaran O'Driscoll, Dublin (IE)

(73) Assignees: Medherant Limited, Coventry (GB); Bostik SA, Colombes (FR)

( * ) Notice: Subject to any disclaimer, the term of this patent is extended or adjusted under 35 U.S.C. 154(b) by 0 days.

(21) Appl. No.: 15/772,951

(22) PCT Filed: Nov. 2, 2016

(86) PCT No.: PCT/GB2016/053388
§ 371 (c)(1),
(2) Date: May 2, 2018

(87) PCT Pub. No.: WO2017/077284
PCT Pub. Date: May 11, 2017

(65) Prior Publication Data
US 2018/0318233 A1 Nov. 8, 2018

(30) Foreign Application Priority Data

Nov. 2, 2015 (GB) ..................................... 1519321
Feb. 19, 2016 (GB) ..................................... 1602907

(51) Int. Cl.
| | |
|---|---|
| *A61K 9/70* | (2006.01) |
| *A61K 9/00* | (2006.01) |
| *A61K 31/167* | (2006.01) |
| *A61K 47/34* | (2017.01) |
| *C08G 18/22* | (2006.01) |
| *C08G 18/48* | (2006.01) |
| *C08G 18/75* | (2006.01) |
| *C08G 18/83* | (2006.01) |
| *C09J 175/04* | (2006.01) |
| *A61K 31/192* | (2006.01) |
| *A61K 31/465* | (2006.01) |
| *A61K 31/618* | (2006.01) |
| *A61K 31/196* | (2006.01) |
| *A61K 31/4168* | (2006.01) |
| *A61K 31/485* | (2006.01) |
| *A61K 31/522* | (2006.01) |
| *A61K 31/573* | (2006.01) |
| *A61K 31/60* | (2006.01) |
| *A61K 47/32* | (2006.01) |

(52) U.S. Cl.
CPC .......... *A61K 9/7069* (2013.01); *A61K 9/0014* (2013.01); *A61K 9/7061* (2013.01); *A61K 31/167* (2013.01); *A61K 31/192* (2013.01); *A61K 31/196* (2013.01); *A61K 31/4168* (2013.01); *A61K 31/465* (2013.01); *A61K 31/485* (2013.01); *A61K 31/522* (2013.01); *A61K 31/573* (2013.01); *A61K 31/60* (2013.01); *A61K 31/618* (2013.01); *A61K 47/32* (2013.01); *A61K 47/34* (2013.01); *C08G 18/222* (2013.01); *C08G 18/227* (2013.01); *C08G 18/4825* (2013.01); *C08G 18/755* (2013.01); *C08G 18/837* (2013.01); *C09J 175/04* (2013.01)

(58) Field of Classification Search
CPC .............................. C09J 175/08; C09J 175/06
See application file for complete search history.

(56) References Cited

U.S. PATENT DOCUMENTS

| | | | |
|---|---|---|---|
| 5,858,395 A | * | 1/1999 | Shikinami ............ A61K 9/7023 424/449 |
| 7,332,540 B2 | | 2/2008 | Theelen et al. |
| 2004/0181196 A1 | * | 9/2004 | Pickup ................. A01K 11/005 604/305 |
| 2008/0114098 A1 | | 5/2008 | Griswold et al. |
| 2011/0052912 A1 | | 3/2011 | Poivet et al. |
| 2011/0104488 A1 | * | 5/2011 | Mussig ................. C09J 123/02 428/355 EN |
| 2011/0151253 A1 | | 6/2011 | Laferte et al. |
| 2015/0184043 A1 | | 7/2015 | Goubard et al. |
| 2015/0184045 A1 | | 7/2015 | Goubard et al. |

FOREIGN PATENT DOCUMENTS

| | | |
|---|---|---|
| EP | 0 482 554 A2 | 4/1992 |
| EP | 2 336 208 A1 | 6/2011 |
| EP | 2 235 133 B1 | 7/2011 |
| EP | 2468783 A1 | 6/2012 |
| EP | 2682444 A1 | 1/2014 |
| EP | 2865728 A1 | 4/2015 |
| EP | 2 889 348 A1 | 7/2015 |

(Continued)

OTHER PUBLICATIONS

International Search Report issued in PCT/GB2016/053388 dated Feb. 7, 2017 (4 pages).
Written Opinion of the International Searching Authority issued in in PCT/GB2016/053388 dated Feb. 7, 2017 (6 pages).
Cheol Hyun Kim et al: "Controlled drug release of silicone-based adhesive-containing cross-linked siloxane powders as a reservoir", Journal of Applied Polymer Science, vol. 132, No. 26, Mar. 21, 2015 (Mar. 21, 2015) (8 pages).

*Primary Examiner* — Jeffrey C Mullis
(74) *Attorney, Agent, or Firm* — Osha Bergman Watanabe & Burton LLP

(57) ABSTRACT

The invention relates to a silyl-containing polymer that is used, together with a tackifying resin to form an adhesive composition capable of storing and delivering drugs to the skin of a user. Typically the composition is formed into a patch which shows excellent adhesion to the skin even when drugs and other additives are dissolved into the composition.

33 Claims, 9 Drawing Sheets

(56) References Cited

FOREIGN PATENT DOCUMENTS

| EP | 2 889 349 A1 | 7/2015 |
|---|---|---|
| WO | 2007/145996 A2 | 12/2007 |
| WO | 2008/060506 A2 | 5/2008 |
| WO | 2013/136108 A1 | 9/2013 |

\* cited by examiner

DRUG DELIVERY COMPOSITION CONTAINING SILYL POLYMERS

FIELD OF INVENTION

The invention relates to the use of compositions for delivery of drugs to the skin, compositions and patches comprising said compositions for drug delivery to the skin, methods of drug delivery to the skin and methods of making said patches and compositions.

BACKGROUND OF THE INVENTION

Drug delivery systems for the skin have been on the market for many years in order to treat a range of different conditions. Common examples of drugs which are often administered to the skin include nicotine to help smokers quit smoking, analgesics to provide targeted pain relief and hormones to provide contraception and replacement therapy. The two main approaches which currently exist for this kind of drug delivery are patches and gels.

One of the problems associated with drug delivery patches is that they are frequently unable to adequately store and convey the desired active agents onto, into and/or through the skin. This problem is not as commonly observed with gel compositions. However, gel compositions are often messy to use and/or do not promote gradual diffusion of active agents. The drugs contained within the gels are imparted to the skin quickly and so do not provide a prolonged therapeutic effect. It is also difficult to control the dosage of drugs when using gels.

Accordingly, it is desirable to provide a system, preferably a patch system, which is capable of not only storing and transmitting active compounds to the skin but that does so with a suitable diffusion profile over time so as to ensure maximum effectiveness of the delivered compounds during a certain time period. The system should ideally have good adhesion to the skin to keep the system in place but be easily removable causing little discomfort and leaving no residues.

WO 2013/136108 discloses compositions containing silyl-containing polymers together with tackifying resins which are used to make breathable adhesives. These find applications in a wide range of industries including automotive, construction and medical applications. However, no mention is provided regarding the drug storing abilities of these materials.

US 2011/0151253 and US 2011/0052912 also disclose compositions containing silyl functionalised polyurethane compositions which are used as adhesives. However, there is no indication regarding other possible applications or properties of the compositions beyond their adhesive qualities. Similar compositions are also described in US 2015/0184045 and US 2015/0184043.

Compositions comprising silylated polymers have been considered before as drug delivery systems, see for instance WO 2008/060506. However, such materials suffer from poor adhesion when drugs are incorporated into the materials and/or fail to adequately dissolve drugs and/or are restricted to a narrow range of drugs which are capable of being solubilised.

The present invention is intended to overcome or at least ameliorate some of these problems.

SUMMARY OF INVENTION

There is provided, in a first aspect of the invention, a composition for drug delivery to the skin comprising: a cross-linked silyl-containing polymer and at least one drug for drug delivery to the skin. The inventors have found that polymers containing silyl groups crosslink very well and act as excellent carriers for transdermally delivered drugs. In particular, silyl groups have been found to crosslink well with other silyl groups in adjacent polymer chains, especially when curing occurs in the presence of water.

It is typically the case that the polymers have two or more silyl groups. Whilst only one silyl group is required for crosslinking to occur between adjacent polymer chains, it has been found that having two or more improves the degree of cross-linking that can occur. The amount of cross-linking can be varied by increasing the number of silyl groups thus allowing the skilled person to tailor the required level of cross-linking to suit a particular application (e.g based on dosage of drug to be carried, the duration over which the drug is required to be released, the particular type of drug being carried, etc).

It is also typically the case that the polymers further comprises a least one group adapted to dissolve or disperse the at least one drug for drug delivery to the skin. The polymers may be functionalised to contain a variety of functional groups in order to imbue the polymer with various properties to improve the characteristics of drug delivery. In particular, monomer units or pendent moieties may be incorporated into the polymer which improve the solubility or disperability of a given drug to be delivered. Depending on the drug to be delivered and the drug delivery profile required, a range of monomer units and functional groups can be introduced to provide the desired characteristics. For instance, the polymer may include moieties of polyethylene glycol within its structure in order to increase hydrophilicity.

Typical examples of silyl-containing polymer include: silyl-containing polyethers, silyl-containing polyurethanes, silyl-containing polyesters, co-polymers thereof and/or combinations thereof.

There is no particular restriction on the type of co-polymers used in the invention however, the copolymers are typically block copolymers, random copolymers, alternating copolymers, graft copolymers or combinations thereof. Typically, the polymers are block copolymers.

In addition, it is typically the case that the silyl-containing polymer has a structure according to general formula (I), (II), (III) or (IV):

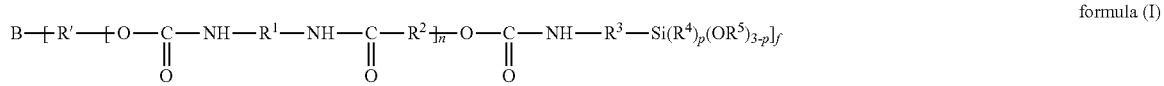

formula (I)

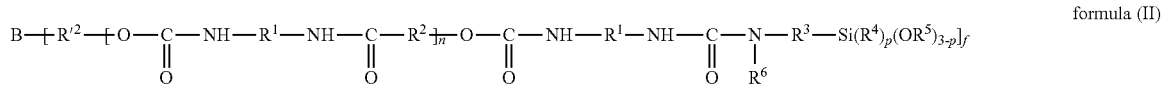

formula (II)

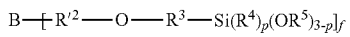 formula (III)

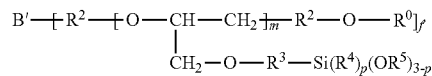 formula (IV)

wherein:
B represents a divalent or trivalent group;
R¹ represents a hydrocarbon-based group;
R² and R'² each independently represent a polyether, polyester or combination thereof;
R³ represents a hydrocarbon-based group;
R⁴ and R⁵ are each independently selected from a linear or branched alkyl, group;
R⁶ represents a hydrogen or a hydrocarbon-based group;
R⁰ represents a hydrocarbon-based group;
B' represents a hydrogen atom or a mono, di or trivalent radical of formula IVa

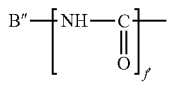 (IVa)

wherein B" is a hydrocarbon-based radical comprising 1 to 20 carbon atoms and one or more heteroatoms selected among O, N, S and Si;
n is an integer greater than or equal to 0;
f is an integer equal to 2 or 3;
f' is an integer equals to 1, 2 or 3; and
p is an integer equal to 0, 1 or 2;

Wherein n, f and f' are selected such that the number-average molecular weight of the polymer of formula (I), (II), (III) or (IV) is greater than 700 Da.

Unless otherwise pointed out, the various substituents which are defined above in formulae (I), (II), (III) and (IV) keep the same definition throughout the present text.

As B is either a divalent or trivalent group, the polymer of the invention has either two or three pendent chains attach to B, each of which comprises a group having the following structure:

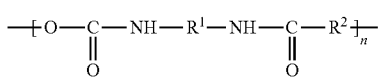

The value of "n" for each of these groups (referred to hereafter as n', n" and n"') sums to the total "n" value described above. In other words:

$$n'+n''+n'''=n$$

wherein n"' is optional, depending on whether B is a divalent or trivalent group. Each of n', n" and n"' is an integer and may be equal to zero.

It may be the case that, where B is divalent, B together with R'² (i.e. R'²—B—R'²) is a polyether or polyester. Similarly, it may be the case that, where B is trivalent, B together with R'² (i.e. B—(R'²)₃) is a polyether or polyester.

It is often the case that B is selected from compounds having a formula according to formula (IIIa) or (IIIb):

(IIIa)
$$D\begin{matrix}R'^2\\ \diagdown\\ R'^2\end{matrix}$$

(IIIb)
$$T\begin{matrix}R'^2\\ —R'^2\\ \diagdown\\ R'^2\end{matrix}$$

wherein "T" and "D" are each independently selected from a linear, branched, cyclic, aromatic, alicyclic, saturated or unsaturated hydrocarbon radical comprising 2 to 66 carbon atoms which may contain one or more heteroatoms; Typically, T and D are each independently selected from: linear, branched, cyclic, aromatic, alicyclic, saturated or unsaturated hydrocarbon radicals comprising 2 to 10 carbon atoms and may include one or more oxygen heteroatoms. In some instances, T and D may be derived from a triol or diol respectively, by deletions of the 2 hydroxy groups. For instance, D is the divalent group derived from 1,2-ethanediol by deletion of the 2 hydroxyl groups, and T is the trivalent group derived from glycerol (1,2,3-propanediol) by deletion of the 3 hydroxyl groups.

Typically, R¹ represents a hydrocarbon-based group comprising in the range 5 to 15 carbon atoms, such as, typically an aromatic or aliphatic, linear, branched or cyclic alkyl group.[1]

Typically, R² and/or R'² may each be a polyester. Where R² and/or R'² are a polyester (typically a divalent polyester group), the polyester typically includes two terminal hydroxyl groups. The polyesters are generally chosen from aliphatic and aromatic polyesters (e.g. amorphous, semi-crystalline or crystalline type) or mixtures of these compounds. Examples that may be mentioned include polyesters resulting from the condensation of: at least one aliphatic diol (linear, branched or cyclic, saturated or unsaturated) or aromatic diol, such as ethanediol, 1,2-propanediol, 1,3-propanediol, 1,4-butanediol, 1,6-hexanediol, fatty alcohol dimers, glycerol, trimethylolpropane, 1,6-hexanediol, 1,2,6-hexanetriol, triethanolamine or N-methyldiethanolamine with:

at least one polycarboxylic acid or ester or anhydride derivative thereof such as 1,6-hexanedioic acid, dodecanedioic acid, azelaic acid, sebacic acid, adipic acid, 1,18-octadecanedioic acid, fatty acid dimers, phthalic acid, succinic acid, and mixtures of these acids, an unsaturated anhydride such as maleic or phthalic anhydride, or a lactone such as caprolactone.

Among these polyesters, mention may thus be made of the following commercial products:

Tone® 0240 (available from the company Union Carbide) which is a polycaprolactone with a molecular mass of about 2000 Da, of $I_{OH}$ equal to 56, having a melting point of about 50° C.;

Realkyd XTR 10410 (available from the company Cray Valley), with a molar mass of about 1000 Da, of $I_{OH}$ equal to 112 and which is a liquid product with a viscosity of 1000 ml' a-s at 35° C.;

Dynacoll® 7381 with a molecular mass of about 3500 Da, of $I_{OH}$ equal to 30, and with a melting point of about 65° C.;

Dynacoll® 7360 with a molecular mass of about 3500 Da, of $I_{OH}$ equal to 30, and with a melting point of about 55° C.;

Dynacoll® 7330 with a molecular mass of about 3500 Da, of $I_{OH}$ equal to 30, having a melting point of about 85° C.;

Dynacoll® 7363 with a molecular mass of about 5500 Da, of $1_{OH}$ equal to 21 and with a melting point of about 57° C.

Additionally, $R^2$ and/or $R'^2$ are a polyether (typically a divalent polyether group). The polyethers are typically chosen from aliphatic polyethers and aromatic polyethers. The polyether generally comprises a plurality of oxyalkylene repeating units, preferably oxyethylene, oxypropylene and/or oxybutylene.

As examples of aliphatic polyethers, mention may be made of oxyalkyl derivatives of diols (such as ethylene glycol, propylene glycol, neopentyl glycol), and polytetramethylene glycols.

According to a preferred embodiment of the invention, the divalent polyether radical is chosen from the group selected from: polyoxyethylenes, polyoxypropylenes polyoxybutylenes, and block or statistical copolymeric mixtures thereof, and also block or statistical copolymeric mixtures of polyoxyethylenes, polyoxybutylenes, and polyoxypropylenes.

Preferably, the polyether is chosen from the group formed by generally statistical or block copolymers formed from ethylene oxide and propylene oxide. Alternatively, the polyether may be polypropylene glycol.

The divalent polyether radicals are preferably, according to the invention, polypropylene glycols, polytetramethylene glycols and polyethylene/polypropylene glycols (copolymers generally having a block or statistical structure).

As is known to those skilled in the art, the polyethers may be prepared by ring-opening polymerization of a cyclic compound comprising oxygen such as a compound chosen from the group formed by ethylene oxide, propylene oxide, butylene oxide, often in the presence of an initiator such as a monomeric diol.

More preferably, the polyether is a polypropylene glycol. Typically, $R^2$ and/or $R'^2$ are a polyether.

Typical examples of polyester and polyether groups are described in U.S. Pat. No. 8,906,192.

Typically, $R^3$ represents a divalent linear or branched alkylene group which typically comprises in the range 1 to 10 carbon atoms, or more typically in the range 1 to 3 carbon atoms. It is typically the case that $R^3$ is an alkylene group.

Usually, $R^4$ and $R^5$ are each independently selected from a linear or branched alkyl group which typically have in the range 1 to 10 carbon atoms, or more typically 1 to 4 carbon atoms.

Typically, $R^6$ represents a hydrogen atom; a linear, branched, cyclic, aromatic alkyl or alkylene group typically have in the range 1 to 30 carbons. More commonly, $R^6$ represents a hydrogen atom or a linear, branched, cyclic, aromatic alkyl group having in the range of 1 to 10 carbons. Typically, $R^6$ represents a hydrogen atom, an aliphatic radical or a phenyl radical. Often, $R^6$ represents a hydrogen atom.

Typically, f is equal to 2.

Typically, p is an integer equal to 0 or 1.

It is often the case that, n, f and f' are selected such that the number-average molecular weight of the 20 polymer in formula (I) and (II) is in the range 700 Da and 250 kDa, typically in the range 6000 Da to 50 kDa. Further, "n" may be equal to zero.

The cross-linked matrix that results from cross-linking the above mentioned polymers has been found by the inventors to be particularly effective at storing compounds for drug delivery to the skin and also releases compounds gradually over a prolonged period of time. Further, the adhesive properties of the composition are not compromised by the addition of drugs or other common additives.

The composition is a mixture of at least one drug; and the silyl-containing polymer described above which, when reacted (typically in the presence of a catalyst), forms a cross-linked polymer matrix. Accordingly, the invention is intended to encompass compositions containing a drug and the cross-linked polymer matrix resulting from the reaction between the above silyl-containing polymers.

Accordingly, there is also provided, a composition for drug delivery to the skin, wherein the composition comprises a first component obtainable by cross-linking a silyl-containing polymer (typically in the presence of a catalyst) as described above; and a second component comprising at least one drug.

Examples of typical silyl-containing polymers suitable for use with the invention are disclosed in EP 2 235 133, EP 2 468 783, EP 2 865 728, EP 2 889 349, WO 2013 136108 and EP 2 889 348. In particular, those silyl-containing polymers described in EP 2 889 349 and EP 2 889 348.

It is typically the case that the composition includes a compatible tackifying resin. This improves the adhesive properties of the composition and allows the composition to be formulated into a pressure sensitive adhesive (PSA). Compositions including a compatible tackifying resin provide good adhesion to the skin and can be removed effectively leaving negligible residue. This is particularly surprising as, although many applications are known for these materials (See WO 20131136108), drug delivery is not specifically disclosed and the main application currently is for bonding glass to various substrates e.g. in the construction industry. Without being bound by theory, it is speculated that a synergistic interaction between the silyl-containing polymers described above and the tackifying resin occurs which minimises the reduction in adhesive qualities when compounds are solubilised in the material.

The ratio of tackifying resin to silyl-containing polymer is typically in the range 1:10 to 10:1, more typically, 1:2 to 2:1 and is typically about 1:1. The composition typically comprises: a) from 20 to 85% by weight, more typically 30 to 60% by weight of at least one silyl-containing polymer as described above; and b) from 15 to 80% by weight, or more typically 30 to 60% by weight of at least one tackifying resin. Typically the composition comprises about 50% silyl-containing polymer and about 50% tackifying resin.

The composition of the invention is intended to deliver drugs "to the skin". By, "to the skin" it is meant that the drugs are administered either: onto the surface of the skin; into the skin; or delivered to the body transdermally i.e. through the skin and into the blood stream.

The term "drug" as used herein is intended to refer to a biologically active substance. There is no particular limitation on the type of compound from which the drug is made. The drugs used with the present invention are typically molecules with low molecular weight, especially where the drug is intended for transdermal delivery. However larger molecules and macromolecules are also envisaged including biological compounds such as peptides and proteins. The term "drug" is also intended to encompass pharmaceutically acceptable salts of biologically active substances. It is also envisaged that the drug may provide a physical effect on the body, such as heating or cooling, which may have a therapeutic effect.

The term, "small molecule drugs" is intended to encompass those compounds typically produced by synthetic chemical processes having a molecular weight typically less than 1000 Da, more typically less than 700 Da.

The term "polymer" is intended to refer to macromolecules comprised of a plurality of repeating monomer units, typically having a weight average molecular weight of greater than 600 Da, preferably greater than 2000 Da.

The term "cross-linked" as used herein is intended to refer to the covalent interconnection of polymers within a compositions either directly (polymer to polymer) or indirectly (polymer to intermediate bridging group to polymer) typically as a result of a reaction between particular polymer side groups and other corresponding side groups on adjacent polymers or intermediate bridging groups. This may be achieved using a catalyst and/or with the presence of co-reactants, such as water. Further, elevated temperatures, radiation such as ultraviolet (UV) radiation or electron-beam (EB) radiation may be used to promote the cross-linking reaction. Where a catalyst is used, at least one catalyst is typically present in the composition in an amount in the range 0.001 to 5% by weight, more typically 0.01 to 3% by weight of the composition. The catalyst may remain in the composition or may be used up in the crosslinking process.

The term "curing" as used herein is to be understood as "cross-linking" (as described above) the components of a composition together until the desired properties of the cured material are achieved. This cross-linking in the present invention typically occurs between silyl groups of the silyl-containing polymers described above.

It is typically the case, that the silyl-containing polymers describe above will have a weight average molecular weight in the range 700 Da to 250 kDa, more typically from 6 kDa to 100 kDa and even more typically from 10 kDa to 50 kDa.

The dispersity of the silyl-containing polymers is typically less than 3, more typically less than 2 and is most typically in the range 1.0 to 1.6, typically 1.1 to 1.4.

According to one embodiment of the invention, the silyl-containing polymers of formula (I) wherein n equals 0 (described above) may be obtained by a step a0) of reacting a polyether polyol with a quantity close to stoichiometry of an alpha-, beta- or gamma-isocyanatosilane The isocyanatosilane reacts quantitatively with any residual polyether polyol in order to form the silane derivative of said polyol. Said derivative contributes to the cross-linking reaction of the silyl-containing polymer. Said derivative can react with the silyl-containing polymer to form a three dimensional network comprising siloxane links.

In another embodiment of the invention, the silyl-containing polymers of formula (I) wherein n is other than 0 (described above) may be obtained by:
a1) a first step of reacting diisocyanate with a stoichiometric excess of polyether polyol in order to form a polyurethane-polyether having at least two terminal —OH groups; and then b1) a second step of reacting the resulting product with a quantity close to stoichiometry of an alpha-, beta- or gamma-isocyanatosilane.

During the second step b1), the isocyanatosilane reacts quantitatively with any residual polyol remaining from the first step a1), in order to form the silane derivative of said polyol. Said derivative contributes to the cross-linking reaction of the silyl-containing polymer. Said derivative can react with the silyl-containing polymer to form a three dimensional network comprising siloxane links.

In another embodiment of the invention, the silyl-containing polymers of formula (H) (described above), in particular wherein n is other than 0 may be obtained by the following process:
a2) reacting a polyether polyol with a stoichiometric excess of diisocyanate, in order to form a polyurethane-polyether having at least two terminal —NCO groups; and b2) reacting the product of step a2) with a quantity close to stoichiometry of an alpha-, beta- or gamma-aminosilane.

During step b2), the aminosilane reacts quantitatively with any residual diisocyanate remaining from step a2), in order to form the silane derivative of said diisocyanate. Said derivative contributes to the cross-linking reaction of the silyl-containing polymer. Said derivative can react with the silyl-containing polymer to form a three dimensional network comprising siloxane links.

In another embodiment of the invention, the silyl-containing polymer of formula (I) may be obtained by the following process:
a3) reacting a polyether polyol with a stoichiometric excess of diisocyanate, in order to form a polyurethane-polyether block having at least two terminal —NCO groups;
b3) reacting the polyurethane obtained in step a3) with a polyester polyol, in order to form a polyurethane having polyurethane-polyether and polyurethane-polyester blocks comprising at least two terminal blocks consisting each in a polyurethane-polyester block having a terminal —OH group; and
c3) reacting the polyurethane of step b3), with a quantity close to stoichiometry of an isocyanatosilane.

Typically, the polyether polyols are selected from aliphatic and aromatic polyether polyols. More typically, the mean molecular mass of the polyether polyols is in the range 500 Da to 20 kDa and typically the average number of hydroxyl functional groups per mole of polyether polyol is in the range 1.0 to 4.6, typically in the range of 2.0 to 4.6.

Typical aliphatic polyether polyols include oxyalkyl derivatives of: diols, such as ethylene glycol, propylene glycol, neopentyl glycol; triols, such as glycerol, trimethylolpropane, and hexane-1,2,6-triol. Mixtures thereof may also be utilised.

The polyether polyols may be selected from polyethers derived from the condensation of diol monomers or a mixture of polyethers deriving from the condensation of diol monomers with up to 30% by weight of polyethers deriving from the condensation of triol monomers.

It may be the case that the polyether polyol is a polypropylene glycol which may have an average number of hydroxyl functional groups per mole of polyether polyol in the range 2.0 to 3.0. For example, the polyether polyol may be selected from:

Voranol® EP 1900: difunctional polypropylene glycol (PPG) having a molecular weight of about 3800 Da and a hydroxyl index $I_{OH}$ of 28 mg KOH g$^{-1}$;

Voranol® CP 755: trifunctional PPG having a molecular weight of about 700 Da and a hydroxyl index $I_{OH}$ of 237 mg KOH g$^{-1}$, both available from Dow Company®;

PPG ACCLAIM® 6300: trifunctional PPG ACCLAIM® 6300 having a molecular mass of about 6000 Da and an $I_{OH}$ of 28.3 mg KOH g$^{-1}$;

ACCLAIM® 8200 N: difunctional PPG having a number average molecular mass of 8000 Da and an $I_{OH}$ of 13.5 mg KOH g$^{-1}$;

ACCLAIM® 12200: difunctional PPG having a number average molecular mass of 12000 Da and an $I_{OH}$ of 10 mg KOH g$^{-1}$;

ACCLAIM® 18200: difunctional PPG having a number average molecular mass of 18000 Da and an $I_{OH}$ of 6.5 mg KOH g$^{-1}$.

The composition comprising the polyether polyol used in steps a0), a1), a2) and a3) described above can further comprise one or more chain extenders selected from diols and polyamines which typically have a molecular mass ranging from 60 to 500 Da.

Examples of diols include: ethylene glycol, propylene glycol, diethylene glycol, dipropylene glycol, 3-methyl-1,5-propanediol, 1,4-butanediol, 1,6-hexanediol, 2-ethyl-1,3-hexanediol, N,N-bis(hydroxyl-2-propyl)aniline, 3-methyl-1,5-pentanediol, or combinations thereof.

Examples of polyamines include: ethylene diamine, diphenyl methane diamine, isophorone diamine, hexamethylene diamine, diethyltoluene diamine, or combinations thereof.

Typically, the diisocyanate used in steps a1), a2) and a3) may have the following formula (V):

NCO—R$^1$—NCO  (V)

wherein R$^1$ is defined as above and is preferably selected from:

(1)

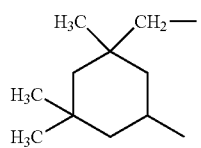
(2)

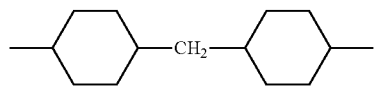
(3)

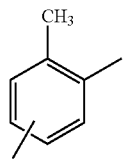
(4)

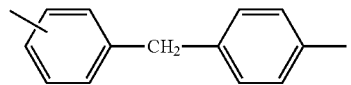
(5)

Typically, the diisocyanate is isophorone diisocyanate (IPDI).

During the first step a2) or a3) described above of the process, it is often the case that the polyether polyol is reacted with an excess of diisocyanate. This means that the quantity of both reactants of step a) or i) corresponds to an excess of the equivalent number of —NCO groups (present in the quantity of diisocyanate) in comparison to the equivalent number of —OH groups (present in the quantity of polyether polyol) increased, if appropriate, by the equivalent number of —OH, —NH2, and/or —NH groups present in the diol and/or the diamine used as a chain extender.

Typically, those quantities correspond to an equivalent ratio —NCO/OH ranging from 1.3 to 5.0. Said ratio is defined as being equal to the equivalent number of —NCO groups divided by the equivalent number of —OH, —NH2, and/or —NH regarding functional groups brought by the corresponding quantities of both reactants, which are the diisocyanate on one hand and the other the mixture of polyether polyols comprising, if appropriate, a chain extender. The quantities by weight of the reactants to be fed into the reactor are determined on the basis of this ratio, as well as, regarding the polyether polyols, on the hydroxyl index $I_{OH}$. The hydroxyl index $I_{OH}$ is the number of hydroxyl functional groups per gram of polyether polyol, said number being expressed, in particular in the present application, in the form of the equivalent number of milligrams of KOH used in the dosage of hydroxyl functional groups. When the diisocyanate is an aliphatic diisocyanate, the step a1), a2) or a3) is often carried out in the presence of a catalyst, preferably chosen from organometallic salts such as organometallic salts or complexes of lead, cobalt, iron, nickel, titanium, bismuth, zinc, tin, such as for example dibutyltin dilaurate (DBTL), titanium tetraisopropylate or bismuth/zinc carboxylates.

The appropriate quantity of diisocyanate is introduced into the appropriate quantity of polyether polyol which is previously fed into the reactor of step a1), a2) or a3), said step being preferably performed at a temperature from 50° C. to 100° C.

According to step b2), the polyurethane obtained from step a2) reacts with an alpha, beta or gamma amino silane of formula (VI):

R$^6$—NH—R$^3$—Si(R$^4$)$_p$(OR$^5$)$_{3-p}$  (VI)

wherein R$^6$, R$^3$, R4 and R$^5$ are such as defined previously.

Preferably, in formula (VI), R$^6$ represents a hydrogen atom or a C1-C10 aliphatic or aromatic hydrocarbon group which can be linear, branched or cyclic; R$^3$ represents a linear alkylene divalent radical comprising from 1 to 3 carbon atoms; R$^4$ and R$^5$, which are identical or different, each represents a linear or branched alkyl group having 1 to 4 carbon atoms, with the possibility, when there are several R$^4$ (or R$^5$) groups, that these groups are identical or different; p is an integer equal to 0, 1 or 2.

It is often the case that an aminosilane of alpha type (corresponding to R$^3$ representing the divalent radical: —CH$_2$—) or of gamma type (corresponding to R$^3$ representing the divalent radical: —(CH$_2$)$_3$—) is used, because of its commercial availability.

Examples of aminosilanes described above include:
Alpha-aminosilane
having the formula (VII):

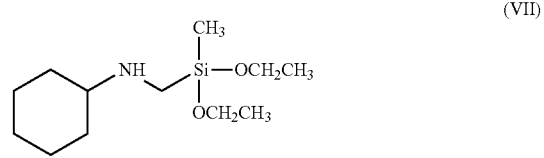 [SMILES: CCO[Si](C)(CNC1CCCCC1)OCC]
(VII)

having a molar mass of 245.5 g, available from Wacker Chemie AG Company under the trader name Geniosil® XL 924.

Alpha-aminosilane having the formula (VIII):

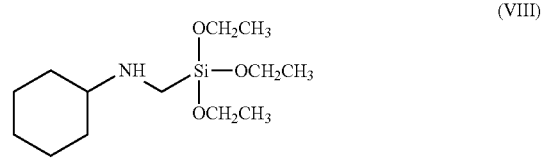 [SMILES: CCO[Si](CNC1CCCCC1)(OCC)OCC]
(VIII)

having a molar mass of 275.5 g, available from Wacker Chemie AG Company under the trade name Geniosil® XL 926.

Gamma-aminosilane having the formula:

having a molar mass of 235 g, available from Evonik Degussa Company under the trade name Dynasylan® 1189.

Gamma-aminosilane having the formula:

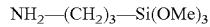

having a molar mass of 179.3 g, available from Momentive Company under the trade name Silquest® A-1110.

Gamma-aminosilane having the formula:

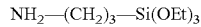

having a molar mass of 221.1 g, available from Momentive Company under the trade name Silquest® A1100.

Preferably, a gamma-aminosilane of formula (VI) wherein $R^5$ represents an ethyl group is used for the improved stability to moisture of the corresponding silyl-containing polyurethane.

Advantageously, the quantity of aminosilane which reacts with the polyurethane obtained from step a2) corresponds to an equivalent ratio of mole number —NCO/mole number of aminosilane ranging from 0.95 to 1.0.

Practically, the corresponding quantity of aminosilane introduced into the reactor is calculated from the mole number of —NCO groups comprised in the polyurethane obtained from step a2). This number, which is calculated and/or determined by analysis of the polyurethane, comprises terminal —NCO groups of the polyurethane and the —NCO groups of isocyanate monomer which have not reacted at step a2). The excess of aminosilane ensures the reaction of all the NCO functions present in the products present during step a2), including the functions of isocyanate monomers having not reacted during the poly condensation reaction of step a2). The term "polyol" is intended to encompass those groups terminating in a hydroxy functionality and encompasses compounds other than alcohols, such as carboxylic acid groups, which also terminate in a hydroxy group. However, it is typically the case that the hydroxy group is an alcohol hydroxy group.

Typically, step b2) is performed at a temperature ranging from 40 to 100° C. At the end of step b2), the silyl-terminated polyurethane is obtained.

The polyurethane-polyether block having —NCO terminal groups obtained at the end of step a3) reacts with a polyester polyol, according to step b3) of the process.

The polyester polyols are chosen from aliphatic or aromatic polyester polyols, and mixtures thereof. Usually, their average molecular mass is ranged from 1 to 10 kDa, more preferably from 2 to 6 kDa, and their hydroxyl functionality can vary from 2 to 4.

Examples of polyols include: polyester polyols of natural origin such as castor oil; polyester polyols resulting from condensation of; one or more aliphatic (linear, branched or cyclic) or aromatic alcohols such as ethanediol, 1,2-propanediol, 1,3-propanediol, glycerol, trimethylolpropane, 1,6-hexanediol, 1,2,6-hexanetriol, butenediol, triethanolamine, N-methyldiethanolamine and mixtures thereof with, one or more polycarboxylic acid or its ester or anhydride derivative such as 1,6-hexanedioic acid, dodecanedioic acid, azelaic acid, sebacic acid, adipic acid, 1,18-octadecanedioic acid, phthalic acid, succinic acid, and mixtures of those acids, a unsaturated anhydride such as maleic or phthalic anhydride, or a lactone such as caprolactone.

Typically, the polyols are difunctional i.e. comprise two terminal hydroxy groups. Usually, the monomers of the polyols are also difunctional and are typically diols.

Examples of typical polyester polyols that can be used in the process for manufacturing according to step b3), include the following products having a hydroxyl functionality equal to 2:

KURARAY® Polyol P-1010, available from Kuraray Company, which is derived from condensation of adipic acid and 6-methyl-1,5-pentyl diol having a molecular weight of 1000 Da, a hydroxyl number of 112, and being liquid at room temperature;

TONE® 0240 (available from Union Carbide) which is a polycapro lactone having a molecular weight of about 2000 Da, an $I_{OH}$ equal to 56, and a melting point of about 50° C.;

DYNACOLL® 7381 having a molecular weight of about 3500 Da, an $I_{OH}$ equal to 30, and a melting point of about 65° C.;

DYNACOLL® 7360 which derives from condensation of adipic acid with hexanediol, a molecular weight of about 3500 Da, an $I_{OH}$ equal to 30, and a melting point of about 55° C.;

DYNACOLL® 7330 having a molecular weight of about 3500 Da, an $I_{OH}$ equal to 30, and a melting point of about 85° C.;

DYNACOLL® 7363 which derives from condensation of adipic acid with hexanediol, having a molecular weight of about 5500 Da, an $I_{OH}$ equal to 21 and a melting point of about 57° C.;

Usually, the polyester polyol used is a polycaprolactone, castor oil or a polyester polyol resulting from the condensation of ethanediol, 1,3-propanediol and/or 1,6-hexanediol with the adipic acid and/or phthalic acid.

Typically, the polyester polyol used in step b3) has a —OH functionality ranging from 2 to 3, a functionality of 2 being often used.

During step b3), the polyurethane reacts with an excess of polyester polyol in term of equivalent functional groups. Preferably, the reactant quantities correspond to an —NCO/—OH equivalent ratio ranging from 0.10 to 0.80, said equivalent ratio being defined as previously. The quantities by weight of reactants to be fed into the reactor are determined on the basis of this ratio, as well as, regarding polyester polyol, on their hydroxyl index $I_{OH}$ whose definition is identical, mutatis mutandis, to the definition previously given for the polyether polyols.

Typically, the polyester polyol used in step b3) has a melting point superior or equal to 55° C., corresponding to a significant crystallinity. In such a way, the "green strength" of the polyurethane obtained in the end is improved.

It is typically the case that, for step b3), the appropriate quantity of polyester polyol is introduced into the appropriate quantity of polyurethane previously fed into the reactor. The reaction is preferably carried out at a temperature from 70 to 110° C.

According to steps b1) or c3), the polyurethane having —OH terminal groups obtained in the end of, respectively, steps a1) or b3) reacts with an isocyanatosilane of formula (IX):

 (IX)

wherein $R^3$, $R^4$, $R^5$ and p are as defined previously:

According to step a0) the polyether polyol also reacts with an isocyanatosilane of formula (IX).

In formula (IX), preferably $R^3$ represents a linear alkylene divalent radical comprising from 1 to 3 carbon atoms; $R^4$ and $R^5$, which are identical or different, each represents a linear or branched alkyl group having 1 to 4 carbon atoms, with the possibility, when there are several $R^4$ (or $R^5$) groups, that these groups are identical or different;

p is an integer equal to 0, 1 or 2.

Typical examples of isocyanatosilanes include gamma-isocyanato-n-propyl-trimethoxysilane available under the trade name Geniosil® GF 40 or the alpha-isocyanato-methyl-dimethoxymethylsilane available under the trade name Geniosil® XL-42, both available from Wacker Company.

Typically, the quantities of isocyanatosilane and either of polyether polyol (implemented in step a0)) or of polyurethane having —OH terminal groups (implemented during steps b1) and c3)) correspond to an equivalent ratio —NCO/—OH ranged from 0.95 to 1.05. It is often the case that step c3) is conducted at a temperature of about 100° C.

As regards the tackifying resin(s) which are included in the composition of the invention, the expression "compatible tackifying resin" means a tackifying resin which, when it is mixed in 50%/50% by weight proportions with the silyl-containing polymer gives a substantially homogeneous blend.

According to one embodiment of the invention, the tackifying resin is selected from: phenol modified terpene resins (typically polyterpenes), hydrocarbon resins (typically where the hydrocarbons have an aromatic character, i.e. comprise one or more aromatic groups), rosin ester resins, modified rosin ester resins and acrylic resins. Typically, the phenol modified terpene resins have a softening point from, 70° C. to 150° C., or more typically 110° C. to 130° C.; the hydrocarbon resins have a softening point in the range 10° C. to 150° C. and more typically 70° C. to 120° C.; and the rosin ester resins have a softening point in the range 10° C. to 130° C., more typically 90° C. to 110° C.

The softening point of the silyl-containing polymer and/or of the tackifying resin can be measured according to ASTM E28 standard.

The tackifying resins are typically compatible with the skin and do not cause irritation, and are substantially non-cytotoxic. Further, the tackifying resins are typically resistant to degradation. Where the tackifying resins do break down over time (e.g. due to photolysis or hydrolysis during use or storage) it is typically the case that the breakdown products are substantially non-toxic and typically do not penetrate the skin.

Typically, the phenol modified terpene resins are obtained by polymerization of terpene hydrocarbons and phenols, in the presence of Friedel-Crafts catalysts.

According to one embodiment, hydrocarbon resins are selected from: resins obtained by a process comprising the polymerization or co-polymerization of [alpha]-methyl-styrene, said process possibly also including a reaction with phenols, resins obtained by hydrogenation, polymerization or copolymerization (with an aromatic hydrocarbon) of mixtures of unsaturated aliphatic hydrocarbons having less than or equal to 10 carbon atoms derived from petroleum fractions, optionally grafted with maleic anhydride, terpene resins, generally resulting from the polymerization of terpene hydrocarbons such as, for example, monoterpene (or pinene) in the presence of Friedel-Crafts catalysts, copolymers based on natural terpenes, for example styrene/terpene, [alpha]-methylstyrene/terpene and vinyltoluene/terpene.

According to one embodiment, rosin ester resins are selected from natural or modified rosins, such as for example the rosin extracted from pine gum, wood rosin extracted from tree roots and their derivatives that are hydrogenated, dimerized, polymerized or esterified by monoalcohols or polyols such as glycerol.

According to one embodiment, the molecular weight of the non-acrylic resins as above-disclosed is less than or equal to 10,000 Da, typically less than or equal to 2,000 Da, more typically les than or equal to 1,000 Da.

An acrylic resin is defined as a polymer or oligomer built with a significant amount of (meth)acrylic and/or (meth)acrylate monomers, usually at least 5% weight/weight (w/w), more often at least 10% w/w, still more usually at least 20% w/w, typically at least 30% w/w in the polymeric chain.

According to one embodiment (meth)acrylic monomers are chosen from acrylic acid, methacrylic acid, methyl acrylate, methyl methacrylate, ethyl acrylate, ethyl methacrylate, butyl acrylate, butyl methacrylate, isobutyl acrylate, isobutyl methacrylate, n-hexyl acrylate, n-hexyl methacrylate, 2-ethylhexyl acrylate, ethylhexyl methacrylate, n-heptyl acrylate, n-heptyl methacrylate, stearyl acrylate, stearylmethacrylate, glycidyl methacrylate, alkyl crotonates, vinyl acetate, di-n-butyl maleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxyethyl methacrylate, hydroxyethyl acrylate, allyl methacrylate, tetrahydrofurfuryl methacrylate, tetrahydrofurfuryl acrylate, cyclohexylmethacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy) ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, polyethylenegly col (400) acrylate, polypropyleneglycol (400) methacrylate, benzyl acrylate, benzylmethacrylate, N-vinyl pyrrolidone or N-vinyl lactam.

Typically, (meth)acrylic monomers have up to 20 carbon atoms, and are typically selected from acrylic acid, methacrylic acid, butyl acrylate, 2-ethylhexyl acrylate and hydroxyethylacrylate.

According to one embodiment, acrylic resins are selected from polymers containing at least one (meth)acrylic function or chain part and at least one hydrocarbon chain part, said polymers can be in the form of copolymers, grafted or reacted or block polymers.

The above described resins have a viscosity measured at 100° C. significantly greater or equal to 100 Pa·s, and less than or equal to 100 Pa·s at 150° C. The acrylate resins may comprise repeating units of at least one hydrocarbon monomer and at least one acrylate monomer. Hydrocarbon monomers are selected from the group consisting of styrene, alpha-methyl styrene, vinyl toluene, indene, methylindene, divinylbenzene, dicyclopentadiene, and methyl-dicyclopentadiene, and polymerizable monomers contained in C5-pyperylenic and C5-isoprene and C9-aromatic available streams from the petrochemical industry. Those hydrocarbon monomers are usually polymerized together in various ratios by cationic polymerization using Lewis acid catalysts. Acrylate monomers have the general formula $R_a$-CH=$CR_b$—$COOR_c$ wherein $R_a$, $R_b$, $R_c$ are independently selected from hydrogen, aliphatic groups, and aromatic groups. Acrylate monomers are selected from the group consisting of methyl acrylate, acrylic acid, methacrylic acid, methylmethacrylate, ethyl acrylate, ethylmethacrylate, butyl acrylate, butylmethacrylate, isobutyl acrylate, isobutylmethacrylate, n-hexyl acrylate, n-hexylmethacrylate, ethylhexyl acrylate, ethylhexyl methacrylate, n-heptyl acrylate, n-heptyl methacrylate, 2-methyl heptyl(meth)acrylate, octyl acrylate, octyl methacrylate, isooctyl(meth)acrylate, n-nonyl(meth) acrylate, iso-nonyl(meth)acrylate, decyl(meth)acrylate, isodecyl acrylate, isodecyl methacrylate, dodecyl(meth)acrylate, isobornyl(meth)acrylate, lauryl methacrylate, lauryl acrylate, tridecyl acrylate, tridecyl methacrylate, stearyl acrylate, stearylmethacrylate, glycidylmethacrylate, alkyl crotonates, vinyl acetate, di-n-butylmaleate, di-octylmaleate, acetoacetoxyethyl methacrylate, acetoacetoxyethyl acrylate, acetoacetoxypropyl methacrylate, acetoacetoxypropyl acrylate, diacetone acrylamide, acrylamide, methacrylamide, hydroxy ethylmethacrylate, hydroxyethyl acrylate, allyl methacrylate, tetrahydrofurfuryl methacrylate, tetrahydrofurfuryl acrylate, cyclohexyl methacrylate, cyclohexyl acrylate, n-hexyl acrylate, n-hexyl methacrylate, 2-ethoxyethyl acrylate, 2-ethoxyethyl methacrylate, isodecyl methacrylate, isodecyl acrylate, 2-methoxy acrylate, 2-methoxy methacrylate, 2-(2-ethoxyethoxy)ethylacrylate, 2-phenoxyethyl acrylate, 2-phenoxyethyl methacrylate, isobornyl acrylate, isobornyl methacrylate, caprolactone acrylate, caprolactone methacrylate, polypropyleneglycol monoacrylate, polypropyleneglycol monomethacrylate, poyethyleneglycol(400)acrylate, polypropyleneglycol(400) methacrylate, benzyl acrylate, benzylmethacrylate, sodium 1-allyloxy-2-hydroylpropyl sulfonate, acrylonitrile, and mixtures thereof.

Typically hydrocarbon monomers are selected among the group of aromatic monomers or polymerizable monomers from the C9-aromatic stream from petrochemical sources; of dicyclopentadiene or polymerizable monomers from the C5-pyperylene or C5-isoprene stream from petrochemical sources.

Usually acrylate monomers are acrylic acid and 2-ethylhexyl acrylate, hydroxyethylacrylate, methacrylic acid, butyl acrylate. Softening point of such resins are typically from room temperature up to 180° C., molecular weights range in weight average is typically from 200 to 25000 Daltons, and acid number typically ranging from 0 to 300 mg KOH $g^{-1}$. Typical resins would have molecular weight less than or equal to 10,000 Daltons, more usually less than or equal to 2,000 Da, most typically less than or equal to 1,000 Da; softening point less than or equal to 150° C., more typically less than or equal to 120° C., most typically ranging from 70 to 120° C.; acid number less than or equal to 150 mg KOH $g^{-1}$, more typically less than or equal to 100 mg KOH $g^{-1}$, most typically from 10 to 100 mg KOH $g^{-1}$.

According to one embodiment, the molecular weight of an acrylic resin is less than or equal to 300,000 when only one resin is present in the composition, usually less than or equal to 100,000, most typically less than or equal to 20,000.

A non-acrylic resin can still contain some acrylic functions in a non-significant quantity, either being part of the polymerization chemical reaction, or as grafted or functionalized groups onto monomers or onto the polymeric chains.

Examples of suitable resins include:

Phenol modified terpene resins: DERTOPHENE® H150 available from DRT company with a molecular weight Mn equal to around 630 Da, DERTOPHENE® T having a molecular weight equal to around 500 Da available from the same company;

Hydrocarbons resins: NORSOLENE® W110 available from Cray Valley, which is obtained by polymerization of alpha-methylstyrene without the action of phenols, with a number-average molecular weight of 1000 Da, and a softening point of 110° C., NORSOLENE® W80 is of the same structure as NORSOLENE® WHO but with a lower molecular weight leading to a softening point of 80° C.;

Rosin ester resins: SYLVALITE® RE 100 which is a pentaerythritol rosin ester available from Arizona Chemical and having a molecular weight Mn of around 1700 Da, Acrylic resins: KOLON® PX95 (available from Kolon Industries Inc.) or Eastman® resin described in U.S. Pat. No. 7,332,540 (formulation 1, table 3 column 14), which are polymers containing at least one (meth)acrylic function or chain part and at least one hydrocarbon chain part, said polymers can be in the form of copolymers, grafted or reacted or block polymers, Acronal® 4F available from the BASF Company, Germany, resulting from polymerization of butyl acrylate monomers.

The curing catalyst that may be used in the composition according to the invention may be any catalyst known to a person skilled in the art for silanol condensation. Examples of such catalysts include organic derivatives of titanium such as titanium acetyl acetonate (commercially available under the name TYZOR® AA75 from DuPont), of aluminium such as aluminium chelate (commercially available under the name K-KAT® 5218 from King Industries), of amines such as 1,8-diazobicyclo[5.4.0]undec-7-ene or DBU.

Optionally, the composition according to the invention may also include, in combination with the silyl-containing polymer, thermoplastic polymers often used in the preparation of HMPSAs, such as ethylene vinyl acetate (EVA) or styrene block copolymers.

The curable composition according to the invention may also comprise up to 3% of hydrolysable alkoxysilane derivatives, as a desiccant, typically a trimethoxysilane derivative. Such an agent advantageously prolongs the shelf life of the composition according to the invention during storage and transport, before the use thereof. Exemplary additives include, [gamma]-methacryloxypropyltrimethoxysilane available under the trade name SILQUEST® A-174 from US Momentive Performance Materials Inc.

The composition according to the invention may also include a plasticizer such as a phthalate like diisononylphthalate (DINP) or a benzoate, a paraffinic and naphthenic oil (such as PRIMOL® 352 from Esso) or else a wax of a polyethylene homopolymer (such as A-C® 617 from Honeywell) or a wax of a polyethylene/vinyl acetate copolymer, or else pigments, dyes or fillers.

Further, an amount of 0.1 to 3% of one or more stabilizers (or antioxidants) is typically included in the composition according to the invention. These compounds are introduced to protect the composition from degradation resulting from a reaction with oxygen which is capable of being formed by action of heat or light. These compounds may include primary antioxidants which trap free radicals and are, in particular, substituted phenols such as IRGANOX® 1076 or IRGANOX® 1010 from Ciba. The primary antioxidants may be used alone or in combination with other secondary antioxidants or UV stabilizers.

There is no particular limitation on the choice of drugs that can be used in conjunction with the composition described above providing that said drugs are soluble in the composition. Although reference is made to "skin" throughout the application, it is contemplated that the composition could be applied to wounds and mucosal membranes (such as eyes and gums) as well. However, typically the composition is applied to the skin.

Whilst there is no particular limitation on the choice of drug, the drug will typically have a molecular weight greater than 100 Da, typically in the range 500 Da to 20,000 Da, more typically 500 Da to 10,000 Da and more typically still 500 Da to 5,000 Da. Often, the range will be 100 Da to 5000 Da, more typically 100 Da to 500 Da. As explained above, low molecular weight drugs are particular desirable for transdermal drug delivery where the drug needs to penetrate the skin in order to enter the blood stream.

Often the drugs will be hydrophilic as this improves the ability of drugs to be absorbed into the blood stream (for transdermal drug delivery). Obviously, the drug must be a compound that is capable of dissolving at least partial within the cross-linked polymer matrix either alone or with the assistance of a co-solvent. Hydrophobic and amphoteric drugs are also envisaged especially for application where drugs are for application to the skin surface.

The drugs described herein are not restricted to small molecule drugs but may also encompass biological compound such as proteins, peptides, enzymes, DNA, RNA, siRNA, antibodies or fragments thereof, vitamins, minerals or combinations thereof.

Other compounds or excipients can be added to improve the effectiveness or distribution profile of the drugs. For instance, dyes, pigments, antioxidants, desiccants, pH buffers to maintain stability of drugs for delivery or the drugs may be encapsulated within carriers such as micelles to improve their delivery further. Polymeric materials other than those described above may also be provided, for instance, in order to modify physical characteristics of the composition.

The drugs used are typically selected from the group consisting of: analgesics, antiinflammatory drugs, hormones, anti-addiction drugs such as nicotine, anti-hypotension drugs, anti-depressants, anti-Alzheimer's drugs, anti-infective, anti-scarring drugs, anti-psychotics, metabolic modulators, pigmentation, nutrients, minerals and vitamins.

It is typically the case that the drug used is an analgesic and may be selected from the group consisting of: capsaicin, isobutylphenylpropanoic acid (ibuprofen), flurbiprofen, methyl salicylate, diclofenac epolamine, levomenthol, salicylic acid, ketoprofen, fenbufen, prilocaine, lidocaine, piroxiam, sufentanil, trolamine, or combinations thereof.

Where the drug is an anti-infective drug, it is typically the case that the drug is an antiviral, antibacterial or antifungal drug and examples of typical anti-infective drugs include chlorhexidine, iodine, silver nitrate, chlorquinaldol or combinations thereof.

Alternatively, the drug used may be a hormone. There is no particular restriction on the particular hormone or combination of hormones that may be used in the present invention. However, typically the hormone is selected from: buprenorphine, clobetasone butyrate, clonidine, dexamethasone, diflucortalone valerate, estradiol, oestrogen, ethinylestradiol, gestodene, hydrocortisone, levonorgestrel, norelgestromin, norethisterone, prednisolone, teriparatide, testosterone, triamcinolone, or combinations thereof.

In another embodiment of the invention, the drug used may be any anti-addiction drug such as nicotine and may also be selected from vitamins, nutrients, minerals, or combinations thereof.

Further example of drugs suitable for use in the composition of the invention include anticancer drugs, especially skin cancer.

A range of excipients and preservatives can be incorporated into the composition of the invention depending on the particular selection of drugs for use in the composition. Excipients can be introduced to modify the drug release properties of the composition or other properties of the composition such as the tackiness or colour of the composition. Some excipients may also have a biological effect on the body, such as caffeine, that synergise with other drugs in the composition to improve the overall effectiveness of the composition. The excipients can also be used to modify the physical characteristics of the composition, including providing heating or cooling effects when applied to the skin or softening the skin using moisturising substances.

The composition may further include a solvent or co-solvent intended to improve the solubility of the drugs used in the composition of the invention. There is no particular restriction on the choice of solvent or co-solvent provided that it is compatible with the composition and improves solubility and/or release of drugs from the composition in use. Typically, the solvent or co-solvent is an organic solvent, typically a substantially nonhazardous organic solvent. The solvent is useful in reducing the viscosity of the polymer composition and therefore can be used to improve incorporation of drugs into the polymer matrix.

It is typically the case that the composition of the invention is in the form of a drug delivery patch. Typically, the patch is a transdermal drug delivery patch. The inventors have found that the claimed composition is capable of forming thin films with excellent drug retention and delivery profiles as well as demonstrating excellent skin adhesion and removal properties. The patches typically comprises a thin layer of the cured composition typically with a thickness of less than 10 mm and usually less than 5 mm. The patches may comprise a layer of the cured composition and at least one substrate layer onto which a layer of the composition is applied. This substrate layer is typically not adhesive on one surface so as to permit application of the patch by hand to a user's skin.

The patch of the present invention has several advantages over existing patch designs. As explained above, many patch adhesives are ineffective at dissolution of certain drugs or do not deliver a dosage over a prolonged period. Accordingly, many patches make use of a separate drug reservoir to perform this function. However, this typically requires additional layers to be incorporated into the patch structure and the drugs often still need to permeate through the adhesive layer to reach the skin. Some designs use a centrally positioned reservoir and a perimeter of adhesive to overcome this problem. However, this often leads to poor surface contact between the reservoir and the skin reducing the effectiveness of the patch and adhesion can often be ineffective. This is not a problem with the present invention as the composition can be formulated in a single layer, provides good adhesion and good drug delivery to the skin.

The patch typically comprises a continuous or semi-continuous layer of the composition as described above sandwiched between two substrate layers. It is usually the case that at least one of the substrate layers is comprised of a releasable material which can be easily separated, typically by hand, from the composition layer prior to application of the patch. The two substrate layers may both be made from a releasable material. This releasable layer or a non-releasable "back liner" may also prevent the composition layer from drying out or leaking drug content when not in use and allows the composition layer to be manipulated more easily.

Typically, one of the layers may be made from a non-releasable material or "back liner" that bonds strongly to the composition layer. A further substrate layer comprising a releasable layer may also be applied to the other surface of the composition layer opposite the back liner layer. This allows the patch to form a plaster-type structure that prevents the composition layer from sticking to surfaces when not in use or a user's clothing when in use.

The substrate is adapted to carry the composition and may be a release liner, a carrier film or web. Often the releasable layer comprises a siliconised surface covering all or substantially all of the surface and/or is made from a siliconised material. The releasable layer may be any polymer film that allows release from the composition layer such as PTFE or similar materials.

There is provided in a second aspect of the invention, a process for preparing the composition according to the first aspect of the invention, comprising: a first step of providing a silyl-containing polymer according to the first aspect of the invention;
a second step of dissolving a drug for delivery to the skin into the first component; and
a third step of curing the resulting mixture.

Alternatively, the drug may be added after the third step of curing the mixture. Typically, however the drug is added before curing.

Typically, a tackifying resin is provided with the silyl-containing polymer in the first step of the process. Further, it is usually the case that a catalyst is provided in either the first, second or third step of process. When the catalyst is added in the second step, this is typically done after the drug for delivery to the skin has been added and typically after any additional additives have been incorporated. It is typically the case that the catalyst is added either at the end of the second step or beginning of the third step. Typically, the catalyst promotes silanol condensation. Typical catalysts include, but are not limited to; organic derivatives of titanium(III), titanium (IV) or aluminium (III), such as aluminium trisacetylacetonate,
titanium tetreaalkoxides such as titanium tetrabutoxide and titanium tetraethoxide; and amines, such as 1,8-diazobicyclo [5.4.0]undec-7-ene.

The third step of curing the polymer is typically done in a humid environment i.e. in the presence of water. According to one embodiment, the composition is cured in a humid atmosphere characterized by its humidity level. The humidity level is typically controlled by an appropriate device typically comprising a humidity generator, sensor and regulatory system. Examples of suitable devices are described for instance in EP 2856 937. Typically, the humidity of the curing step is such that in the range of 1% to 100% of the molecules in the curing atmosphere are water, more typically in the range 2% to 95%, more typically still 5% to 90% and even more typically in the range 10% to 80%, even more typically still 15% to 70%. It is often the case that the humidity is in the range 20% to 50% or even more typically still in the range of 25% to 40%. In some case, the humidity is in the range of 1%-90%, often 1% to 10% and in some cases 2% to 8%.

The second step may include heating the first component to a temperature in the range 30 to 150° C., typically 50 to 130° C. and most typically 70 to 100° C. The second step of the process typically includes a mixing step in order to assist dissolution of the drug and ensure a homogeneous mixture is obtained. This may be done with one or more solvents or cosolvents in order to improve dissolution of drugs into the first component. The solvents and co-solvents suitable for use are described above. Typically, said solvents are substantially free of water to prevent any premature curing.

In addition, preservatives, excipients and other additives may be added to the composition and this is typically done together with the addition of the drug, typically during the second step. The first and/or second step may be conducted in an inert atmosphere.

The curing step is typically performed at a temperature greater than room temperature, typically greater than 20° C., often in the range 20 to 200° C. and more typically in the range 40 to 120° C. Often, the temperature will be in the range 50 to 80° C. and is most typically around 60° C.

Typically, in the second step, once a substantially homogeneous mixture has been obtained, the mixture is applied to a back liner or releasable liner before curing. Typically the mixture
is formed into a layer and may be sandwiched between two back liners or releasable liners or combination thereof. There is no particular restriction on the shape or material of the back liner or releasable layer. The back liner is typically a thin, flexible material usually having a thickness of less than 5 mm and often less than 1 mm. The back liner typically bonds strongly to the composition layer. Typically, examples of releasable materials include siliconised surfaces; polyolefinic films or coatings, such as high density polyethylene or polypropylene; stretchable or deformable films or coatings, such as fluoro silicones or polytetrafluoroethylene; and acetate sheeting.

Although it is typically the case that the drug for drug delivery to the skin is introduced before the composition has been cured, depending on the thermal and chemical stability of the drug to be delivered, the drug may be incorporated after the composition has been cured. The drug may be a solid, liquid or a solution comprising the drug when added to the composition.

There is no particular limitation on the duration of the curing step. The time needed for the curing step may vary to a large extent depending on the weight per unit area of composition deposited on the substrate, on the heating temperature, the humidity and the particular makeup of the composition in question. Typically, the duration of the curing steps is in the range of 1 second to 24 hours and more typically is in the range 5 minutes to 24 hours.

Without being bound by theory, it is believed that this curing step has the effect of creating between the polymer chains, under the action of atmospheric moisture, siloxane-type bonds which result in the formation of a three-dimensional polymer network. The thus cured composition acts as a pressure-sensitive adhesive layer which gives the substrate that is coated therewith desirable adhesive strength and tack.

The process may be a batch process or a continuous process. A continuous process may involve the use of heated rollers and to form and heat the composition and steam jets sprinklers may be used to provide humidity to promote the cross-linking reaction.

There is provided in a third aspect of the invention, use of a composition for drug delivery to the skin, the composition comprising: a cross-linked silyl-containing polymer wherein the
cross-linked silyl-containing polymer is as described above. Typically the composition also includes a tackifying resin as described above.

The inventors have found that compositions comprising the cross-linked silyl-containing polymer are extremely effective at storing and conveying drugs to the skin. This is improved when combined with a tackifying resin as described above which helps adherence to the skin.

The composition implemented in the use according to the third aspect of the invention is typically a drug delivery patch. Typically a patch for drug delivery to the skin.

Typically, the drugs used in the composition of the third aspect of the invention are as described above.

There is provided in a fourth aspect of the invention, a method of treating a disease comprising; providing a composition or patch according to the first aspect of the invention; and applying the composition or patch to a user. Typically, to a user's skin.

There is no particular limitation on the types of disease that can be treated using this method. The only limitation is that the drugs used to treat a particular condition are effective when administered to the skin. Typical applications for the composition of the invention include the treatment of diseases selected from: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof.

Further, the method of treatment of the invention may also be for delivering vaccines and/or for improving wound healing.

There is also provided in a fifth aspect of the invention a composition or patch according to the first aspect of the invention for use in therapy. Typically, the conditions which can be treated with the composition or patches of the invention are: analgesia; hypertension; addiction e.g. to nicotine; hormone imbalance; cancer, such as skin cancer; bacterial, viral or fungal infections, Alzheimer's disease, mood disorders, Parkinson's, metabolic diseases, tissue scarring or combinations thereof. Most typically, the compositions and patches of the invention are for use in treating analgesia.

Further, the composition and patches of the invention may also be used as a means for delivering vaccines and/or as a means to improve wound healing.

The invention will now be described with reference to the following figures and examples.

EXAMPLES

Figure 1:
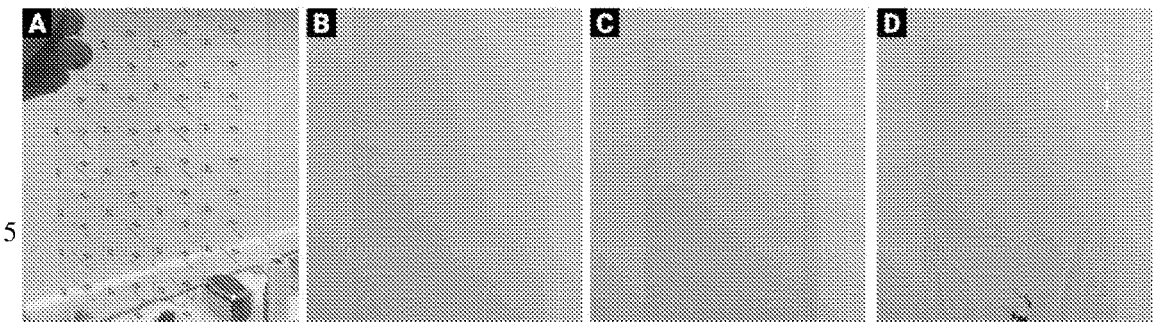
FIG. 1 shows patches loaded with analgesic drugs (5% w/w). Ibuprofen (A), diclofenac epolamine (B), lidocaine (C) and salicylic acid (D).

Preparation of the Polymer Component of the Composition
Description of the Compositions:

Desmoseal® XP2636 is a silane-terminated polyether material (covered by formula (I) with n=0) available from the Company Bayer, Germany, with a viscosity of 35,000 mPa·s at 23° C. (according to ASTM standard D1236), and a tensile strength of 0.77 MPa and elongation at break of 133% in tensile test performed according to standard ISO 37 at room temperature.

SPUR® 1050MM is a silane-terminated polyurethane (covered by formula (I) with n different from 0) available from the Company Momentive, Germany, with a viscosity of 35,000 mPa·s at 23° C. (according to ASTM standard D1236), and a tensile strength of 0.68 MPa and elongation at break of 150% in tensile test performed according to standard ISO 37 at room temperature.

XPS 18446 is produced as described in patent application US20110052912 as polymer A (covered by formula (I) with n different from 0) with a final viscosity of about 55,000 mPa·s (according to ASTM standard D1236), and a tensile strength of 0.83 MPa and elongation at break of 230% in tensile test performed according to standard ISO 37 at room temperature.

Poly 15 (silyl-containing polyurethane-polyether and polyurethane-polyester block copolymer, covered by formula (I) with n different from 0) is produced according to the following process:

Step (a3)—Synthesis of a Polyurethane with 2-NCO End Groups and One or More Polyether Blocks:

In a closed reactor of 250 nil, equipped with a stirrer, heating means, thermometer and connected to a vacuum pump was charged 96.89 g of polyether polyol Acclaim® 12200, having a molecular weight in number of 12000 Da, a hydroxyl number of 10 mg KOH/g (corresponding to an equivalent number of —OH functions equal to 0.178 mmol/g). The material is heated to 80° C. and maintained at a reduced pressure of 20 mbar for 1 hour in order to dehydrate the polyether polyol.

Then, 0.1 g of a bismuth carboxylate/zinc catalyst (Borchi Kat® VP0244 available from Borchers GmbH Company) diluted in methyl ethyl ketone solvent at 90% in weight, and 3.01 g of isophorone diisocyanate (containing 37.6% by weight of NCO functions), are introduced into the reactor. The mixture is maintained at atmospheric pressure and heated to 90° C. The quantities introduced thus corresponding to a ratio NCO/OH equal to 1.56. The polyaddition reaction is allowed to last for 3 hours to obtain 100 g of a polyurethane having a NCO function content (followed by potentiometric titration) equal to 9.71 mmol/g, corresponding to the consumption of all hydroxyl functions originating from initial polyether polyol quantity.

Step (b3)—Synthesis of a Polyurethane Block Polyether and Polyester Terminated with —OH Terminal Groups:

11.52 g of Kuraray® P1010 polyester polyol (having a hydroxyl number of 112 mg KOH/g corresponding to an equivalent OH number function equal to 1.99 mmol/g) is charged in a closed reactor of 250 ml equipped with a stirrer, heating means, thermometer and
connected to a vacuum pump. The material is heated to 80° C. and maintained at a reduced pressure of 20 mbar for 1 hour to dehydrate the polyester polyol. 85.38 g of polyester diol and polyurethane prepolymer obtained in step (a2) is then introduced, thus corresponding to a NCO/OH ratio of 0.6.

The reactor is then maintained under reduced pressure of 20 mbar and heated to 100° C., and polyaddition reaction is progressing for 3 hours until complete consumption of the —NCO polyurethane of step (a2), detected by the progressive disappearing of the NCO peak area by infra-red spectroscopy analysis. This results in 96.9 g of polyurethane with a —OH functions content of 14.74 mmol/g.

Step (c3)—Synthesis of a Polyurethane Block Polyether and Polyester with Alkoxy Silyl Terminal Groups:

3.1 g of gamma-isocyanato-n-propyl-trimethoxysilane (containing 19.9% by weight of NCO functions) is then introduced into the reactor after step (b2) is completed, leading to a mixture where ratio of NCO/OH functions is equal to 1.

The reactor was then kept under inert atmosphere at 100° C. for 90 minutes until complete reaction occurred, detected by the disappearing of the NCO peak area by infra-red analysis. 100 grams of a polyurethane block polyether and polyester with alkoxy silyl end groups are obtained. Viscosity of this resulting material is measured by a Brookfield RTV viscosimeter at 23° C. and at a speed of 20 rpm with a spindle 6, at 70 000 mPa·s.

Poly 5 (silyl-containing polyurethane). This polymer (covered by formula (II)) is prepared according to the following process:

Step (a2)—Preparation of a Polyurethane (CI) Having —NCO Terminal Groups:

Difunctional polypropylene glycol (PPG) having a molecular weight of 4000 Da and a hydroxyl index equal to 28 mg KOH/g was used as a polyether polyol, and isophorone diisocyanate (IPDI) containing 37.6% w/w of —NCO groups (corresponding to an equivalent number of —NCO functions equal to 8.95 mmol/g) was used as the diisocyanate. In a closed reactor of 250 mL, equipped with a stirrer, heating means, a thermometer and connected to a vacuum pump, 84.89 g of polyether polyol are introduced. The reactor is then heated to 80° C.
and maintained under reduced pressure of 20 mbar for 1 hour in order to dehydrate the polyether polyol.

We introduce in the reactor maintained at atmospheric pressure and heated to 90° C. 4.2 mg of a bismuth/zinc carboxylate catalyst (Borchi® Kat VP0244 from Borchers GmbH Company), and 8.70 g of IPDI (containing 37.6% w/w of —NCO group). The quantities introduced correspond to a NCO/OH ratio equal to 1.8. The polyaddition reaction is continued for 4 hours, until entire consumption of the hydroxyl functions of the poly ether polyol. The NCO-content (expressed in % weight/weight) of the product is followed by a potentiometric titration with an amine, until the aimed value of 1.6% w/w is obtained.

Step (b2): Preparation of the Silyl-Containing Polyurethane "Poly5";

We introduce in the reactor in the end of step (a1), 6.40 g of gamma-aminosilane Silquest® A1110, corresponding to a ratio NCO/NR6 equal to 1.

The reactor is then maintained under inert atmosphere at 100° C. for 1.5 hours, until complete reaction is achieved (detected by the disappearance of the NCO-band at infrared analysis).

We obtain 100 g of silyl-containing polymer "poly5" having a viscosity at 23° C. measured by a viscosimeter Brookfield RTV equal to 96 Pa·s.

Poly 3 (Silyl-Containing Polyurethane) Covered by Formula (II):

Step (a2) preparation of a polyurethane (A) —NCO end groups:

Voranol® EP1900 having a hydroxyl index equal to 28 mg KOH/g (corresponding to an equivalent number of —OH function equal to 0.50 mmol/g) was used as the polyether polyol, and an IPDI containing 37.6% w/w of —NCO group (corresponding to an equivalent number of —NCO functions equal to 8.95 mmol/g) was used as a diisocyanate.

In a closed reactor of 250 ml, equipped with a stirrer, heating means, thermometer and connected to a vacuum pump was charged 81.85 g of polyether polyol (i.e.: 40.85 mmol of —OH functions). The mixture is heated to 80° C. and maintained at a reduced pressure of 20 mbar for 1 hour to dehydrate the polyether polyol.

Then, we introduce into the reactor maintained at atmospheric pressure and heated to 90° C.:

0.1 g of a catalyst bismuth/zinc carboxylate (Borchi Kat® VP0244 Borchers GmbH Company) diluted with 90 wt % of MEK and 8.19 g of IPDI (i.e.: 73.32 mmol in NCO—functions).

The quantities introduced thus corresponding to a ratio NCO/OH equal to 1.8. The polyaddition reaction was continued for 4 hours until complete consumption of the hydroxyl groups of the polyether polyol, in order thus to obtain 90.14 g of a polyurethane having —NCO terminal groups, which corresponds to about 32.5 mmol of NCO-functions.

The content of NCO-functions (expressed in % w/w) of the product formed during the reaction is followed by potentiometric titration with an amine, until the target value corresponding to 1.52% is reached.

We then introduce into the reactor, 5.85 g of Unilin® 425 (a linear polymeric monoalcohol of structure C14-054, of IOH=98 mg KOH/g and of melting point=91° C., available from Baker Petrolite), thus corresponding to a NCO/OH ratio equal to 1.44.

The reactor was then kept under inert atmosphere at 100° C. for 1.5 hours until complete reaction is achieved (detected by the disappearance of the NCO-band in the infrared analysis).

This gives 95.98 g of a polyurethane having —NCO terminal group, which represents approximately 22.28 mmol of NCO-functions.

Step (b2) Preparation of Silyl-Containing Polyurethane "Poly3" (Silyl-Containing Polyurethane):

We then introduce into the reactor at the end of step a1), 4 g of aminosilane SILQUEST® A1110 (molecular mass=179 g/mol), thus corresponding to a final NCO/OH ratio equal to 1.

The reactor was then kept under inert atmosphere at 100° C. for 1.5 hours until complete reaction is achieved (detected by the disappearance of the NCO-band in the infrared analysis).

We obtain 100 grams of a silyl-containing polyurethane "poly3". Its viscosity at 50° C. measured by a Brookfield RTV was 57 Pa·s.

SAX® 510 is a silylated polymer of formula (III) wherein $R^3$ represents: —$(CH_2)_3$— and $R^2$ represents a polyether the repeating unit of which is the radical isopropoxy. This polyer is available from Kaneka.

TEGOPAC® BOND 251 is a silylated polymer which is covered by formula (IV) and which is available from Evonik.

Acronal DS3500 is a tackifying resin available from the Company BASF, Germany, comprising methyl acrylate monomers at 91% by weight, and acrylic acid at 9% by weight analyzed by proton and carbon NMR.

Acronal® 4F is a tackifying resin available from the Company BASF, Germany, resulting from polymerization of n-butyl acrylate monomers.

Kolon PX95 is a product from copolymerization of C5-type monomers (68% in weight) with acrylic monomers (acrylic acid 4% in weight, butyl acrylate at 28% in weight analyzed by proton and carbon NMR), available from the Company Kolon Industries, Inc., Korea. It has a softening point of 100° C., an acid number of 20 mg KOH $g^{-1}$ according to analysis test standard ASTM D974, and a molecular weight of 720 averaged in number analyzed by gel permeation chromatography. Its viscosity at 100° C. is significantly higher than 100 Pa·s.

Eastman resin described in U.S. Pat. No. 7,332,540 (formulation 1, table 3 column 14) is a tackifying resin produced as described in patent document U.S. Pat. No. 7,332,540. Its features are exhibited in table 3 columns 14 and 15 as being composed by Styrene monomer at 61% in weight, 2-ethyl-ehexylacrylate at 31% in weight, and acrylic acid at 9% in weight. It also contains less than 2% in weigh of diterbutylperoxide. Its softening point is 100° C., and its acid number is 60 mg KOH/g. Its molecular weight in z-average is 15,000 daltons. Its viscosity at 100° C. is significantly higher than 100 Pa·s 1) Preparation of the Compositions Example 1 to 14 (Composition Described in Table 1 and Table 1bis)

The compositions that appear in the tables 1, 1bis and 1ter below are prepared by firstly introducing the tackifying resin into a glass reactor under vacuum and heating to around 160° C. Then, once the resin is thoroughly molten, the silane-containing polymer is added.

The mixture is stirred under vacuum for 15 minutes, then cooled to 70° C. The catalyst (K-KAT® 5218) is then introduced. The mixture is kept under vacuum and continues to be stirred for another 10 minutes.

The mixture at lab scale is placed in a cartridge closed with two cups and anti-moisture agents to avoid uncontrolled curing.

TABLE 1

| (weight %) | Compositions | | | | | | |
|---|---|---|---|---|---|---|---|
| | 1 | 2 | 3 | 4 | 5 | 6 | 7 |
| Dertophene ® H150 | 48 | | | | | | |
| Norsolene ® W110 | | | | 48 | | | |
| Norsolene ® W80 | | 48 | | | | | |
| Sylvalite ® RE100 | | | 24 | | | | 48 |
| Eastman ® resin | | | | | | | |
| Kolon ® PX95 | | | | | 48 | 33 | |
| Acronal ® 4F | | | 24 | | | | |
| Ac Resin ® DS3500 | | | | | | 15 | |
| XPS ®18446 2-ethylhexyl acrylate monomer acrylic acid melamine formaldehyde ethyl acetate | 50 | 50 | 50 | 50 | 50 | 50 | 50 |
| catalyst | 2 | 2 | 2 | 2 | 2 | 2 | 2 |

TABLE 1bis

| (weight %) | Compositions | | | | | | |
|---|---|---|---|---|---|---|---|
| | 8 | 9 | 10 | 11 | 12 | 13 | 14 |
| Dertophene ® H150 | 48 | 48 | | | | | |
| Sylvalite ® RE100 | | | | | | | 24 |
| Eastman ® resin | | | | | | | 24 |
| Kolon ® PX95 | | | 33 | 33 | 33 | 33 | |
| Ac Resin ® DS3500 | | | 15 | 15 | 15 | 15 | |
| SPUR ® 1050MM | | | 50 | 50 | | | |
| Desmoscal ® XP2636 | 50 | | | | | | |
| "Poly15" | | | | | 50 | | |
| "Poly5" | | | | | | 50 | |
| "Poly3" | | | | | | 50 | 50 |
| catalyst | 2 | 2 | 2 | 2 | 2 | ? | 2 |

TABLE 1ter

| Weight (%) | F15 | F16 | F17 |
|---|---|---|---|
| Compositions | | | |
| Sylvalite RE 100 | 24 | 24 | 24 |
| Norsolène W110 | 24 | 24 | 24 |
| Tegopac<sup>R</sup> Bond 251 | 50 | | |
| SAX<sup>R</sup> 510 | | 50 | |
| Poly 3 | | | 50 |
| Catalyst | 2 | 2 | 2 |

2) Preparation of the tested laminates on PET substrate for technical performance evaluations, said substrates being coated with the cured adhesive composition according to paragraph 1) above, with a coating weight of 20 g/m² at laboratory scale.

As the support layer, use is made of a rectangular sheet of polyethylene terephthalate (PET) having thickness of 50 um and dimensions of 20 cm by 40 cm.

The composition obtained in 1) is preheated to a temperature close to 100° C. and introduced into a cartridge from which a bead is extruded which is deposited close to the edge of the sheet parallel to its width.

The composition contained in this bead is then spread over the entire surface of the sheet, so as to obtain a uniform layer of substantially constant thickness. In order to do this a film spreader (also known as a film applicator) is used, which is moved from the edge of the sheet to the opposite edge. A layer of composition is thus deposited that corresponds to a weight per unit area of 20 g/m², which approximately represents a thickness of the order of 20^m.

The thus coated PET sheet is then placed in an oven at 120° C. for 300 seconds for the curing of the composition, then laminated to a protective non-stick layer consisting of a sheet of siliconized film that is rectangular and has the same dimensions.

The PET support layer thus obtained is subjected to the tests described below.

180° Peel Test on a Stainless Steel Plate 20 Minutes:

The adhesive strength is evaluated by the 180° peel test on a stainless steel plate as described in FINAT method No. 1 published in the FINAT Technical Manual, 6<sup>th</sup> edition, 2001. FINAT is the international federation for self-adhesive label manufacturers and converters. The principle of this test is the following.

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% relative humidity atmosphere. It is then fastened over two-thirds of its length to a substrate constituted of a stainless steel plate. The assembly obtained is left for 20 minutes at room temperature. It is then placed in a tensile testing machine capable, starting from the end of the rectangular strip that is left free, of peeling or debonding the strip at an angle of 180° and with a separation rate of 300 mm per minute. The machine measures the force required to debond the strip under these conditions.

The corresponding results for a coating weight of 20 g/m² are expressed in N/cm and are indicated in table 3.

Tack Test (Also Known as Loop Test or Loop Tack Test):

The tack is evaluated by the loop tack test described in FINAT method No. 9, the principle of which is the following.

A test specimen in the form of a rectangular strip (25 mm×175 mm) is cut from the PET carrier coated with the cured composition obtained previously. This test specimen is, after the preparation thereof, stored for 24 hours at a temperature of 23° C. and in a 50% relative humidity atmosphere. The 2 ends of this strip are joined so as to form a loop, the adhesive layer of which is facing outward. The 2 joined ends are placed in the movable jaw of a tensile testing machine capable of imposing a rate of displacement of 300 mm/minute along a vertical axis with the possibility of moving back and forth. The lower part of the loop placed in the vertical position is firstly put into contact with a horizontal glass plate measuring 25 mm by 30 mm over a square area measuring around 25 mm per side. Once this contact has occurred, the displacement direction of the jaw is reversed. The tack is the maximum value of the force needed for the loop to be completely debonded from the plate.

The corresponding results for a coating weight of 20 g/m² are expressed in N/cm and are indicated in table 3. The failure profile is also indicated in table 3.

Resistance Time of the Adhesive Joint to Static Shear at 23° C.:

The stability of the adhesive strength of the PET carrier coated with the cured composition is evaluated, no later than one hour after it is obtained, by a test which determines the resistance time of the adhesive joint to static shear at 23° C.

Reference is made, for this test, to the FINAT method No. 8. The principle is the following. A test specimen in the form of a rectangular strip (25 mm×75 mm) is cut from the PET support layer coated with the cured composition prepared previously. A square portion of 25 mm per side located at the end of the adhesive strip is fastened to a glass plate. The test plate thus obtained is maintained in a vertical position and the strip left free is connected to a weight of 1 kg. Under the effect of this weight, the adhesive joint which ensures the fastening of the strip to the plate is subjected to a shear stress. To better control this stress, the test plate is in fact placed so as to make an angle of 2° relative to the vertical.

The time taken for the strip to debond from the plate following the rupture of the adhesive joint under the effect of this stress is noted. This time is indicated in the table. The corresponding results for a coating weight of 20 g/m² are shown in table 3.

Resistance Time of the Adhesive Joint to Static Shear at 90° C.:

The same test as before is performed on the adhesives but the test plate submitted to a weight of 1 kg is maintained at a temperature of 90° C. The results for a coating weight of 20 g/m² are shown in table 3.

TABLE 3

Test results for a coating of 20 g m⁻²

| | Peel 180° C. | | Loop tack | | Shear resistance at 90° C. | | Shear resistance |
|---|---|---|---|---|---|---|---|
| | (N/cm) | type of failure | (N/cm) | type of failure | time | type of failure | at 23° C. time |
| 1 | 6.30 | AF | 11.02 | AF | >24 h | | >24 h |
| 2 | 0.94 | AF | 1.38 | AF | >24 h | | >24 h |
| 3 | 0.63 | AF | 2.13 | AF | 70 h | | 14 days |
| 4 | 2.95 | AF | 1.97 | AF | 45 h | | 18 days |
| 5 | 1.61 | AF | 3.98 | AF | 70 h | | 11 days |
| 6 | 2.36 | AF | 3.86 | AF | 70 h | | 8 days |
| 7 | 3.15 | AF | 3.35 | AF | 1 h | AF | 14 days |
| 9 | 6.69 | AF | 10.63 | AF | >24 h | | >24 h |

TABLE 3-continued

Test results for a coating of 20 g m$^{-2}$

| | Peel 180° C. | | Loop tack | | Shear resistance at 90° C. | | Shear resistance at 23° C. |
|---|---|---|---|---|---|---|---|
| | (N/cm) | type of failure | (N/cm) | type of failure | time | type of failure | time |
| 10 | 2.40 | AF | 4.13 | AF | 70 h | | 11 days |
| 11 | 1.57 | AF | 2.0 | AF | >20 min | AF | >4 h |
| 12 | 0.43 | AF | 1.42 | AF | >111 | AF | 14 days |
| 13 | 0.53 | AF | 2.28 | AF | >111 | | 14 days |
| 14 | 1.97 | AF | 2.76 | AF | 6 h | | >24 h |

AF = adhesive failure

Compositions

Three different grades of composition were employed in solubility experiments: A, B and C (see below). A is the grade which was used for initial studies and further was used as the standard grade for solubility tests.

A is a composition according to example 1 of patent EP2235133 specifically incorporated herein by reference.

B is a composition corresponding to a mixture of equal weights of compositions of each of examples 4 and 5 in European patent EP2336208 specifically incorporated herein by reference.

C is a composition according to example 1 of European patent EP2336208 specifically incorporated herein by reference.

F15 is described in table 1ter, it comprises a polymer according to formula (IV).

F16 is described in table 1ter, it comprises a polymer according to formula (III).

F17 is described in table 1ter, it comprises a polymer according to formula (II).

A major difference between these grades is their viscosity at 100° C. Table 1 summarises properties of these compositions.

TABLE 1

Properties of compositions

| Grade | Density, g cm$^{-3}$ | Brookfield viscosity at 100° C., mPa S | Curing conditions |
|---|---|---|---|
| A | 1 | 14000 ± 3000 | Oven at 60° C., 100 |
| B | 1 | 7000 ± 3000 | mL of water in |
| C | 1 | 15000 ± 4000 | vapour phase during |
| F15 | 1 | 1600 ± 500 | 16 hours |
| F16 | 1 | 5000 ± 2000 | |
| F17 | 1 | 2000 ± 500 | |

Typical Patch Preparation Process

A sample of composition is pre-heated to 80° C. in a closed cartridge or inert environment to avoid contact with moisture and approximately 10 ml of the composition is added into a beaker and weighed. A desired quantity of drug, preservative and excipients are then added to the mixture. The mixture is mixed until it has been homogenised and is then cast with the help of a heated Meyer bar onto a release liner. Once cast, the layers of composition are cured at 60° C. in a humid environment during 16 hours.

Drug Release Analysis

Figure 7:
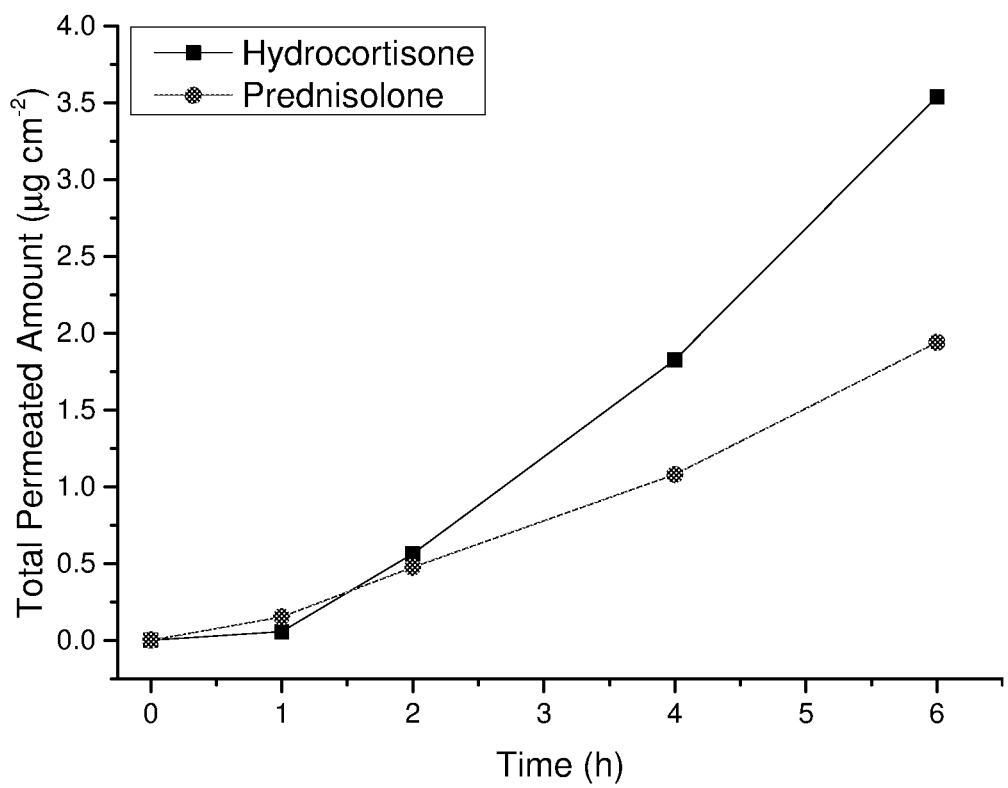
FIG. 7 shows permeation of steroidal drugs across Pion® membranes over time from the patch of the present invention.
Figure 8:
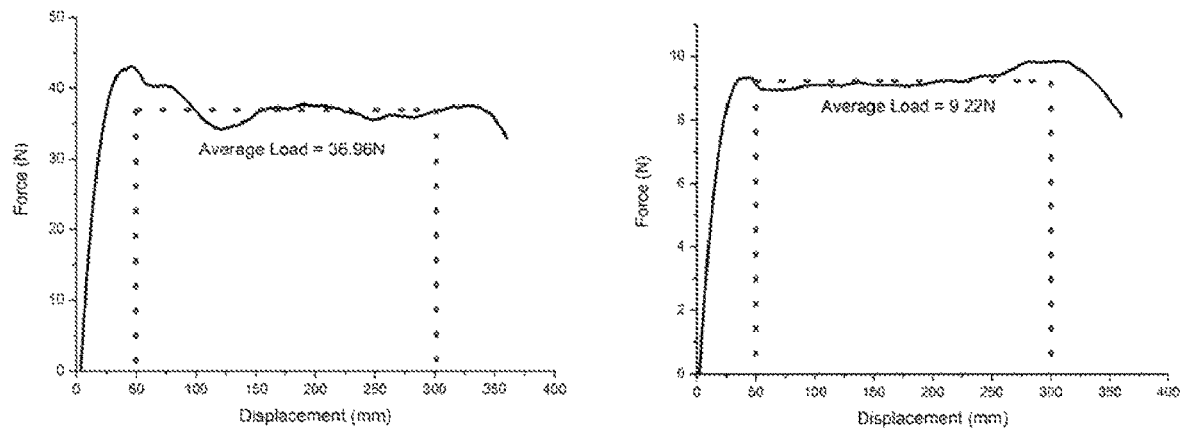
FIG. 8 shows the average load required to peel-off acetate film from pure patches of the invention.
Figure 9:
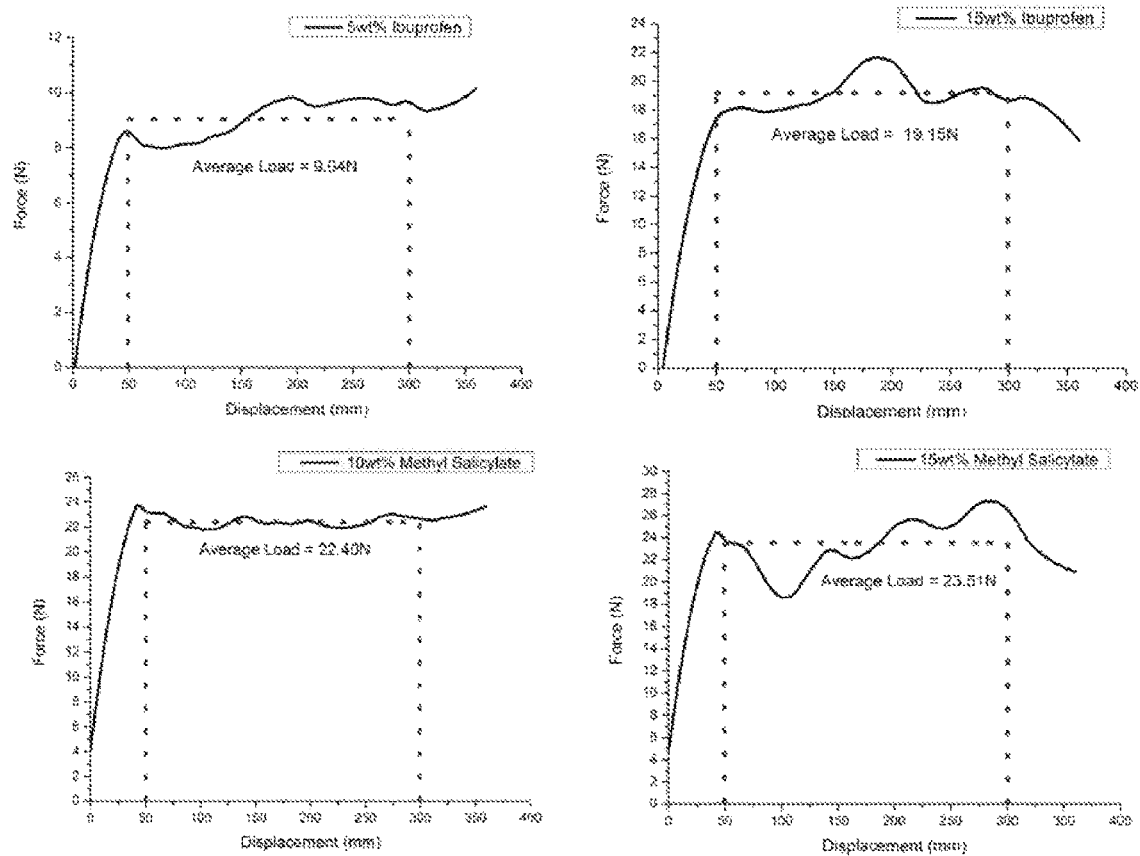
FIG. 9 shows the adhesion of ibuprofen and methyl salicylate patches produced with a grade A composition of the invention.
Figure 10:
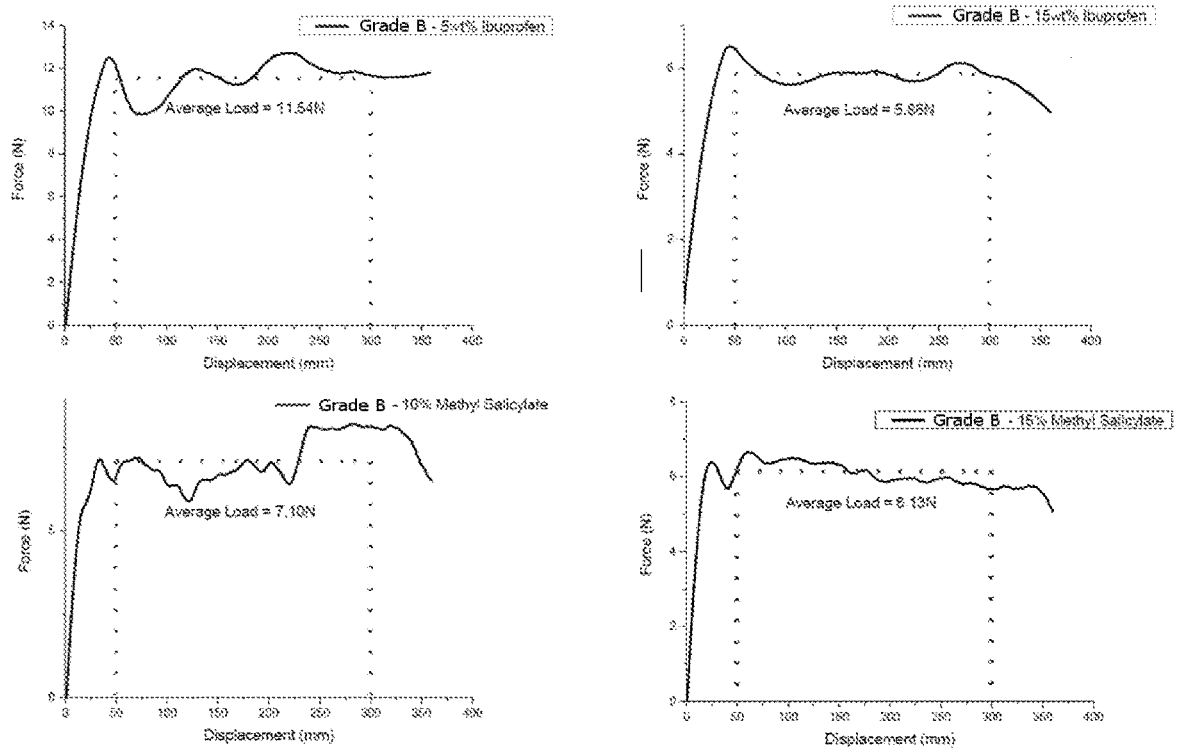
FIG. 10 shows the adhesion of ibuprofen and methyl salicylate patches produced with a grade B composition of the invention.
Figure 11:
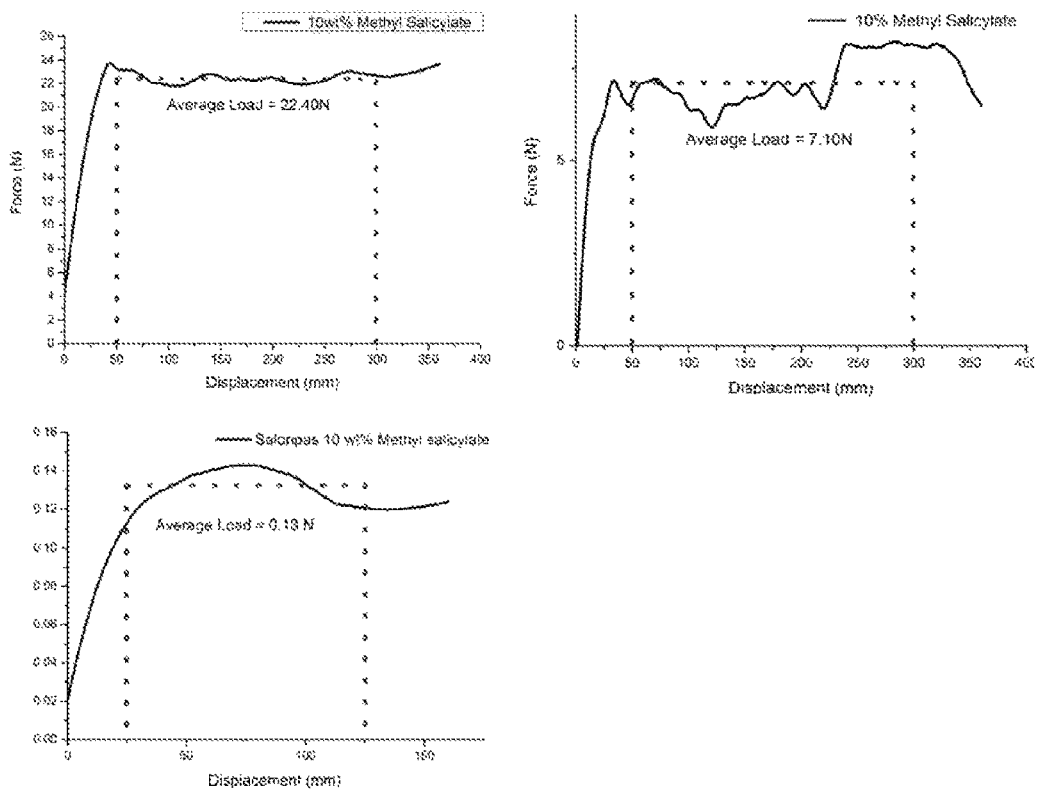
FIG. 11 shows adhesion data for a pre-exiting commercial patch (Salonapas patch) against patches of the present invention using grade A and grade B compositions of the invention (coating 10 wt % methyl salicylate).
Figure 12:
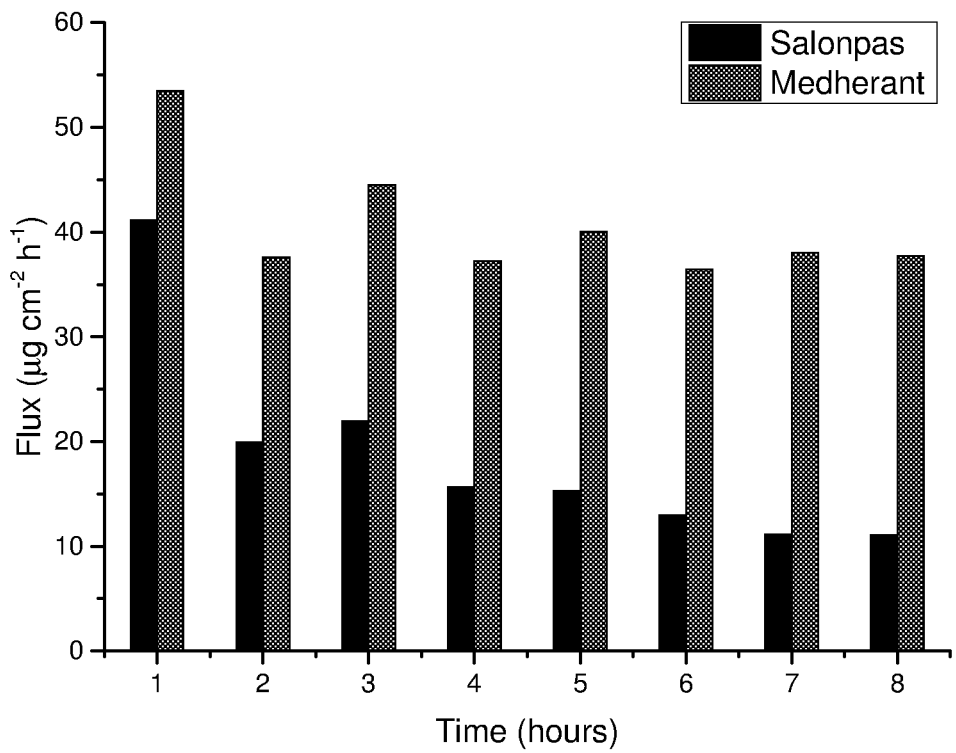
FIG. 12 shows flux of methyl salicylate and menthol through the Pion® membranes from Salonpas (methyl salicylate 10% w/w and menthol 3% w/w, comparative example) patches compared to patches of the present invention (made from compositions of grade A comprising methyl salicylate 10% w/w and menthol 3% w/w)) over each hour after testing.
Figure 13:
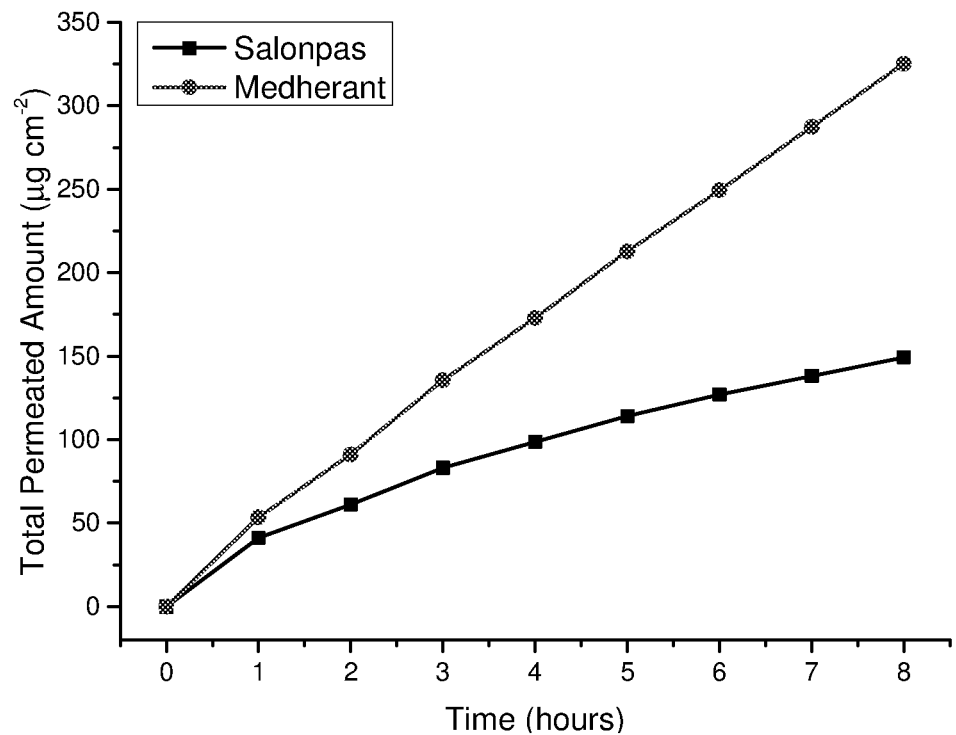
FIG. 13 shows total amount of methyl salicylate and menthol permeated across Pion membranes from Salonpas (methyl salicylate 10% w/w and menthol 3% w/w, comparative example) patches compared to patches of the present invention (made from compositions of grade A comprising methyl methyl salicylate 10% w/w and menthol 3% w/w)) over time.
Figure 14:
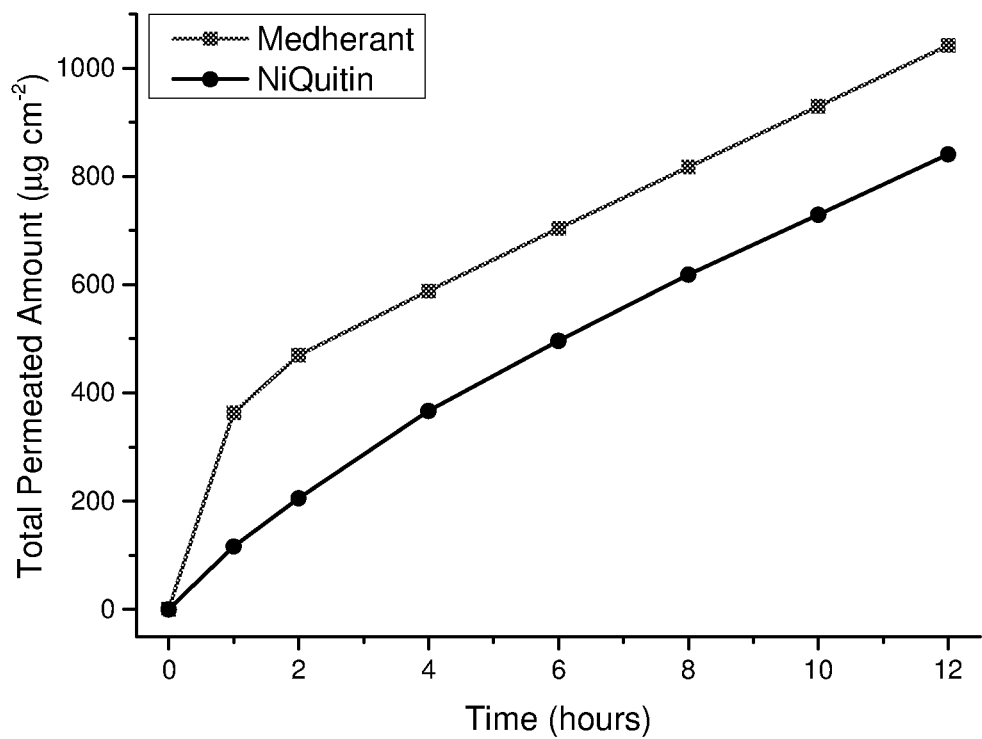
FIG. 14 shows total permeated of nicotine across skin mimicking Strat-M membranes from Niquitin (114 mg) patches compared to patches of the present invention (made from compositions of grade A comprising 49 mg nicotine) over time.
Figure 15:
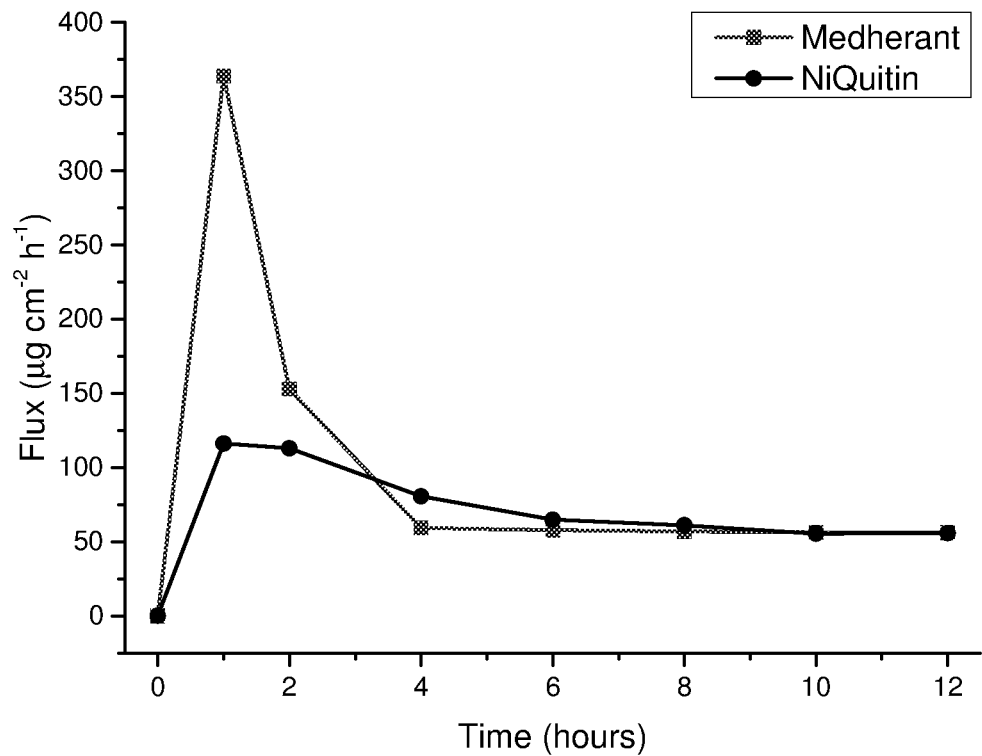
FIG. 15 shows flux of nicotine through skin mimicking Strat-M membranes from Niquitin (114 mg) patches compared to patches of the present invention (made from compositions of grade A comprising 49 mg nicotine) over time.
Figure 16:
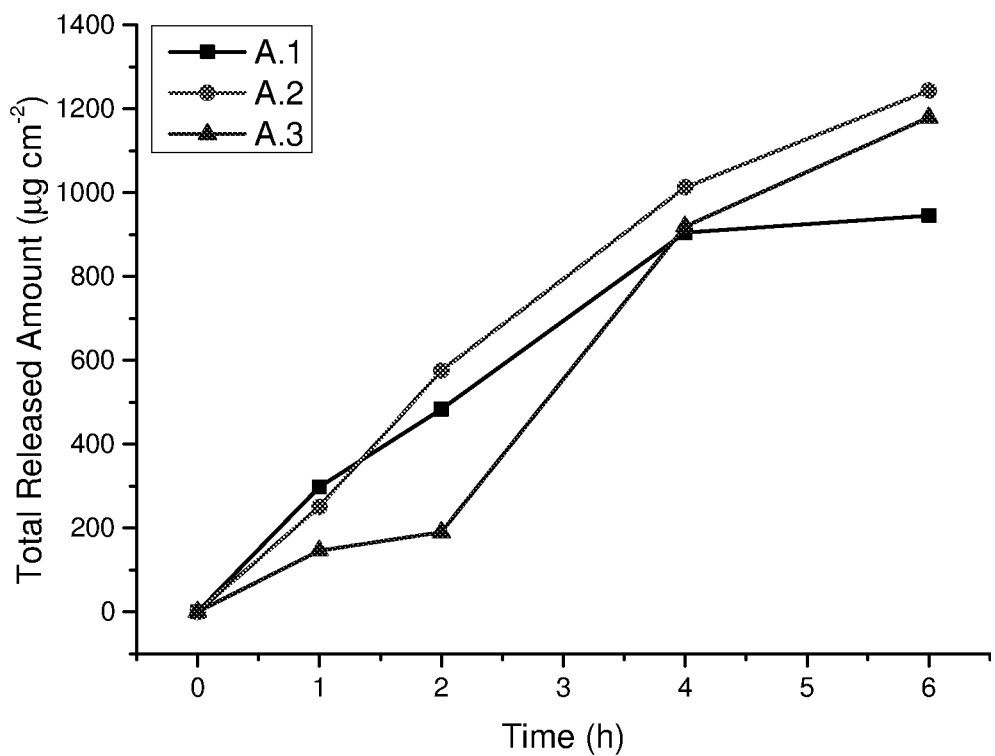
FIG. 16 shows release of ibuprofen through non-rate limiting Nylon membranes from the patches made using grades F15 (A.1), F16 (A.2) and F17 (A.3).
Figure 17:
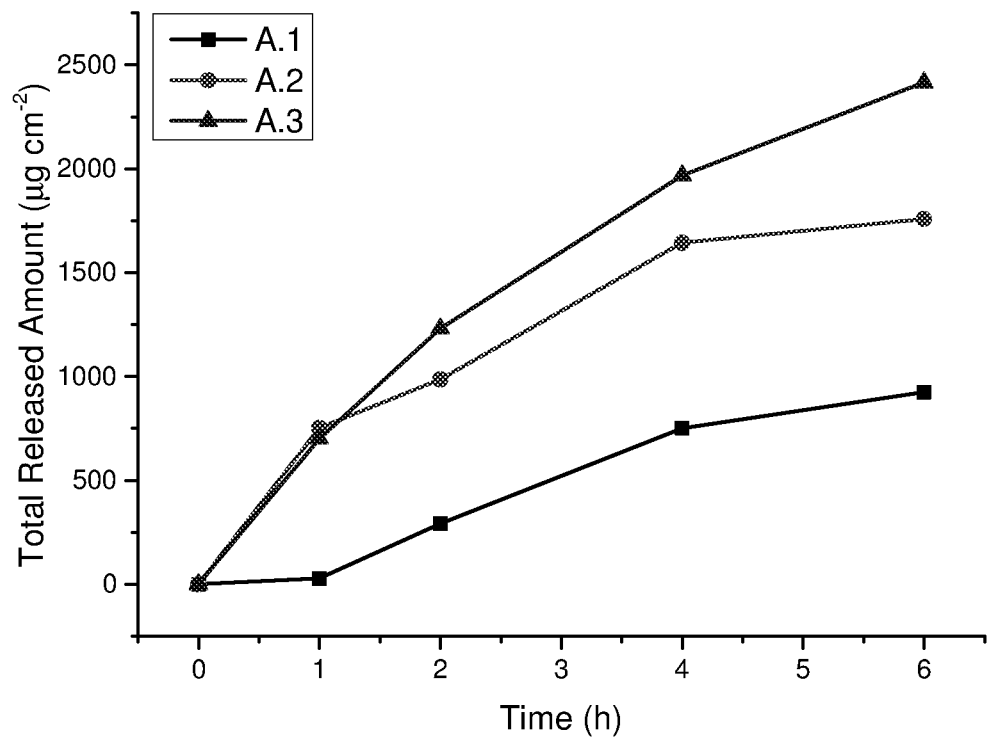
FIG. 17 shows release of lidocaine through non-rate limiting Nylon membranes from the patches made using grades F15 (A.1), F16 (A.2) and F17 (A.3).
Figure 18:
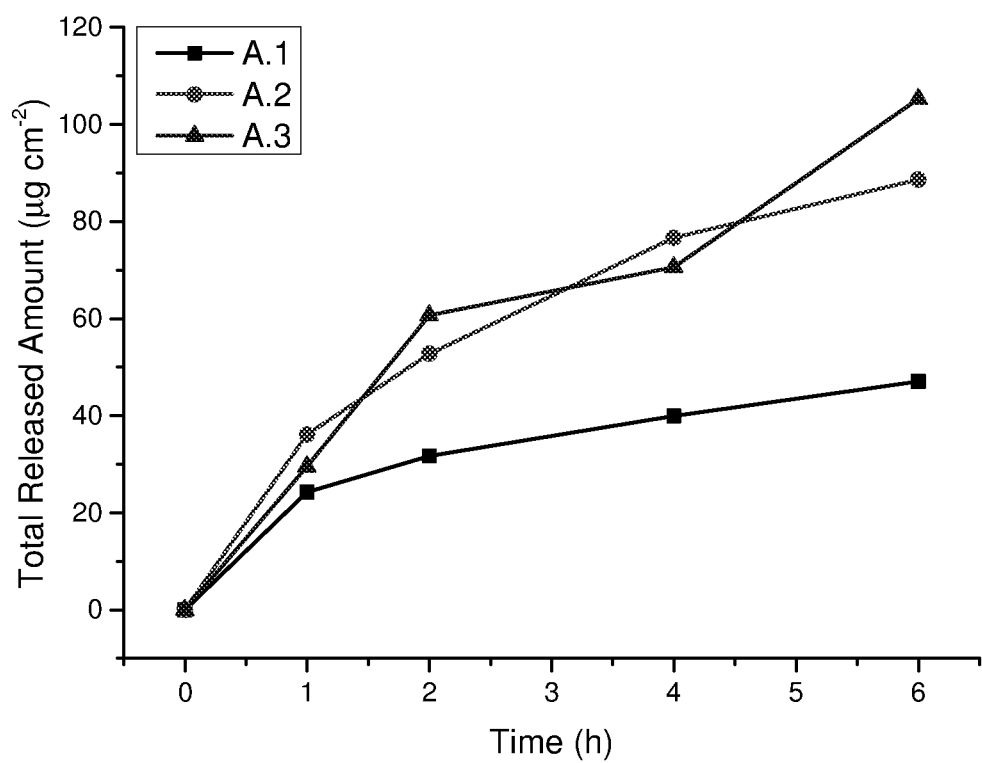
FIG. 18 shows release of methyl salicylate through non-rate limiting Nylon membranes from the patches made using grades F15 (A.1), F16 (A.2) and F17 (A.3).

In order to determine the drug release profile of the manufactured patches, a pre-cut patch was attached to a membrane (typically Pion, Nylon or Strat-M). The membrane and patch are then placed in a Franz cell and then a PBS pH 7.4 buffer solution is added. Samples are taken at one hour interval for 8 hours. The amount of drug released is calculated using a validated HPLC/UV-Vis method depending on the drug in question. Data for the drug release properties of the patches of the invention for a range of drugs are shown table 2 and in FIGS. 7 and 8 below.

TABLE 2

Permeated drug amount. All values are in μg cm$^{-2}$

| | Sample | | | | |
|---|---|---|---|---|---|
| hours | Ibuprofen | Methyl Salicylic | Diclofenac | Salicylic acid | Caffeine |
| 1 | 15.46 | 18.25 | 0.11 | 3.38 | 0.19 |
| 2 | 37.23 | 24.58 | 0.16 | 11.92 | 2.33 |
| 4 | 73.85 | 59.78 | 0.39 | 31.75 | 3.26 |
| 6 | 99.60 | 83.03 | 0.47 | 54.71 | 21.89 |

| | Sample | | | | |
|---|---|---|---|---|---|
| hours | Ketoprofen | Lido-caine | Prednisolone | Hydro-cortisone | Nicotine |
| 1 | 0.90 | 16.81 | 0.06 | 0.15 | 2.26 |
| 2 | 4.59 | 38.49 | 0.56 | 0.47 | 5.05 |
| 4 | 17.37 | 78.43 | 1.83 | 1.08 | 13.76 |
| 6 | 35.67 | 110.02 | 3.54 | 1.94 | 18.33 |

Patch Adhesion Analysis

Figure 5:
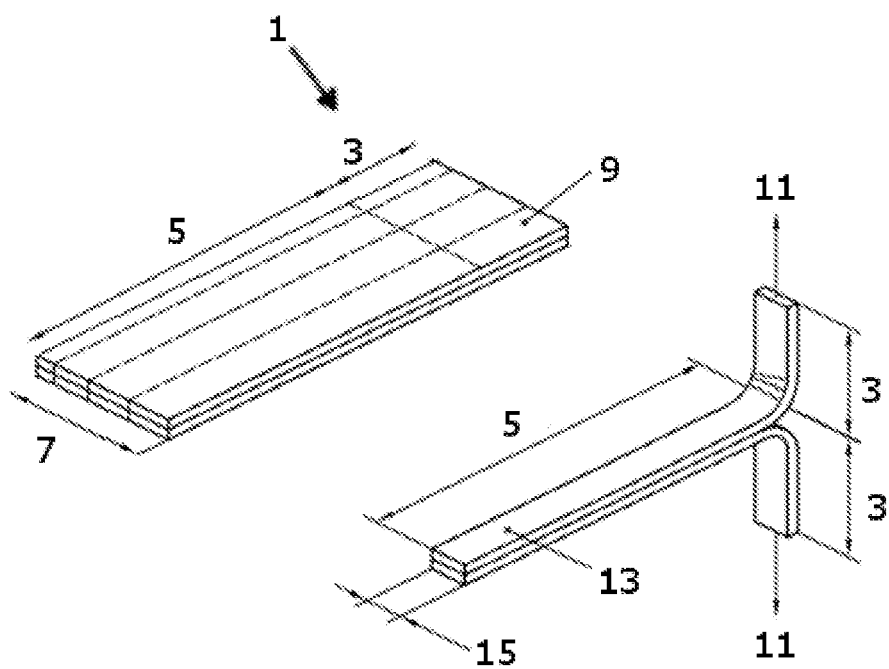
FIG. 5 shows a typical sample used when measuring the "tack" of an adhesive material.
Figure 6:
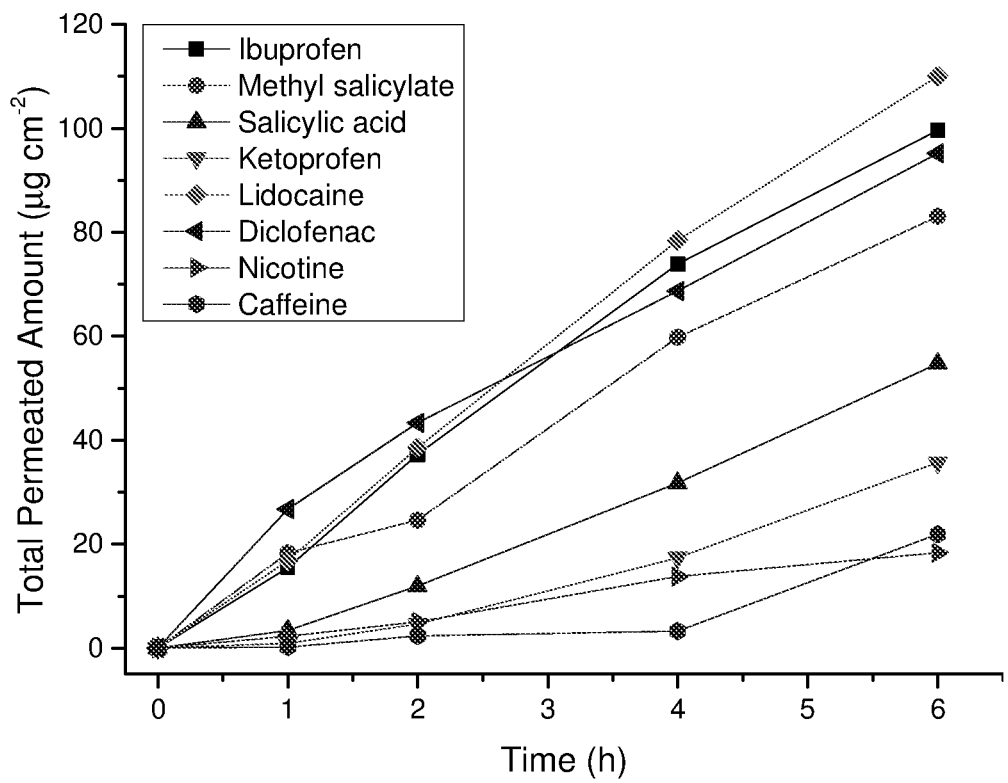
FIG. 6 shows permeation of NSAIDs and other drugs across Pion® membranes over time from the patch of the present invention.

Three specimens 9 were prepared from a sample 1 as shown in FIG. 5 for each measurement. The specimen 9 has a length 5, a width 15 (around one third the width 7 of the sample 1) and consist of two layers 13. The width 15 was 25.4 mm and the length 5 was 350 mm. A first layer made of adhesive material is provided, attached to a second layer of back liner, in this case an acetate film having a thickness of 100 μm. The acetate film is attached to the adhesive layer by roll lamination and allowed to rest for 24 hours before testing. The unbound end 11 of each end of the T-shaped specimen 1 is affixed in a grip (not shown). Each end 11 is aligned correctly to ensure that the tension is applied evenly across the entire specimen 9. The two grips are then drawn apart at a rate of 10 mm min$^{-1}$ with a sample rate of 1000 ms. The test was continued until 180 mm of the bonded length 5 was separated. The back liner to which the composition layer was attached in these experiments was a HHlum thick acetate film. The adhesion results for the exemplary compositions are shown below in FIGS. 9 to 12.

Principles of Formulation

In all experiments benzyl alcohol (BenzOH) was employed as a co-solvent. BenzOH is widely used in both pharmaceutical and cosmetic formulations as a preservative, and therefore its addition is required to improve the shelf life of patches. We also found that it reduces viscosity of adhesives allowing a better and faster homogenisation of the polymer/drug mixtures. Additionally, it acts as a solvent for drugs improving their dissolution in the polymer matrix compositions. The total amount of BenzOH in all formulations was in a range of 1-3% w/w.

An amount of drug added to the composition of the invention was calculated to result in 5% w/w concentration in patches. All compounds in the liquid state were added by volume, which was estimated using their specific densities.

Solubility of Analgesic Drugs

Most of the analgesic drugs tested were molecularly soluble in the standard grade (A) 10 composition. Only fenbufen and prilocaine demonstrated poor solubility, and were rather physically dispersed than dissolved. The inventors have found that ibuprofen, ketoprofen, methyl salicylate, salicylic acid, lidocaine and levomenthol are readily soluble in the standard grade. This in turn means that the concentration in patches can easily be increased from 5 to 30% w/w. Experiments with diclofenac epolamine and piroxicam showed that these 15 compounds have a limited solubility of 5 and ~2.5% w/w respectively. The data obtained is summarised in Table 3.

TABLE 3

Solubility of analgesic drugs in compositions.

| No | Drug | A | Conc., wt % | B | Conc., wt % |
|---|---|---|---|---|---|
| 1 | Ibuprofen | ✓ | >5 | ✓ | >5 |
| 2 | Methyl salicylate | ✓ | >5 | ✓ | >5 |
| 3 | Diclofenac epolamine | ✓ | >5 | ✓ | >5 |
| 4 | Levomenthol | ✓ | >5 | ✓ | >5 |
| 5 | Salicylic acid | ✓ | >5 | ✓ | >5 |
| 6 | Ketoprofen | ✓ | >5 | ✓ | >5 |
| 7 | Fenbufen | x | — | — | — |
| 8 | Prilocaine | x | — | — | — |
| 9 | Lidocaine | ✓ | >5 | ✓ | >5 |
| 10 | Piroxicam | ✓ | ~2.5 | ✓ | ~2.5 |
| 11 | Flurbiprofen | ✓ | >5 | ✓ | >5 |
| 12 | Salsalate | ✓ | >5 | ✓ | >5 |
| 13 | Indomethacin | ✓ | >5 | ✓ | >5 |
| 14 | Aspirin | x | — | — | — |
| 15 | Paracetamol | x | — | — | — |
| 16 | Naproxen | x | — | — | — |

TABLE 4

List of drugs used in solubility experiments.

| No | Drug | Type | Appearance | Solubility in water, mg mL$^{-1}$ |
|---|---|---|---|---|
| 1 | Ibuprofen | Analgesic | Solid | 0.021 |
| 2 | Methyl salicylate | | Liquid | 0.690 |
| 3 | Diclofenac epolamine | | Solid | ~40 |
| 4 | Levomenthol | | Solid | 0.490 |
| 5 | Salicylic acid | | Solid | 2.24 |
| 6 | Ketoprofen | | Solid | 0.051 |
| 7 | Fenbufen | | Solid | n/a |
| 8 | Prilocaine | | Solid | 0.540 |
| 9 | Lidocaine | | Solid | 0.410 |
| 10 | Piroxicam | | Solid | 0.023 |
| 11 | Flurbiprofen | | Solid | 0.025 |
| 12 | Salsalate | | Solid | 0.246 |
| 13 | Indomethacin | | Solid | 0.002 |
| 14 | Aspirin | | Solid | 4.60 |
| 15 | Paracetamol | | Solid | 14.0 |
| 16 | Naproxen | | Solid | 0.016 |
| 17 | Prednisolone | Hormone therapy | Solid | 0.002 |
| 18 | Hydrocortisone | | Solid | 0.320 |
| 19 | β-Estradiol | | Solid | 0.004 |
| 20 | Testosterone | | Solid | 0.023 |
| 21 | Progesterone | | Solid | 0.009 |
| 22 | Chlorhexidine | Anti-infective/ parasitic/ fungal/ biotic | Solid | 0.8 |
| 23 | Iodine | | Solid | 0.33 |
| 24 | Silver nitrate | | Solid | soluble |
| 25 | Chlorquinaldol | | Solid | insoluble |
| 26 | Tetracycline | | Solid | 0.231 |
| 27 | Ivermectin | | Solid | insoluble |
| 28 | Nystatin | | Solid | 0.360 |
| 29 | Praziquantel | | Solid | 0.400 |
| 30 | Amoxicillin | | Solid | 3.43 |
| 31 | Penicillin G | | Solid | 0.210 |
| 32 | Trimethoprim | Other | Solid | 0.400 |
| 33 | Artesunate | Anti-malaria | Solid | 0.056 |
| 34 | Artemisinin | | Solid | insoluble |
| 35 | Nicotine | Other | Liquid | soluble |
| 36 | Cyclosporine | | Solid | insoluble |
| 37 | Methotrexate | | Solid | insoluble |
| 38 | Salbutamol | | Solid | 14.1 |
| 39 | Caffeine | | Solid | 21.6 |
| 40 | Pramipexole | | Solid | 3.9 |

The grade C composition is the most viscous of the tested samples which limits its application for patch fabrication due to the mixing process. All three grades are identical in terms of drug solubility (tested on ibuprofen, methyl salicylate and levomenthol), but the lower viscosity of A and B makes them preferable for patch fabrication.

Photographs of the patches are displayed on FIG. 1.

Figure 2:
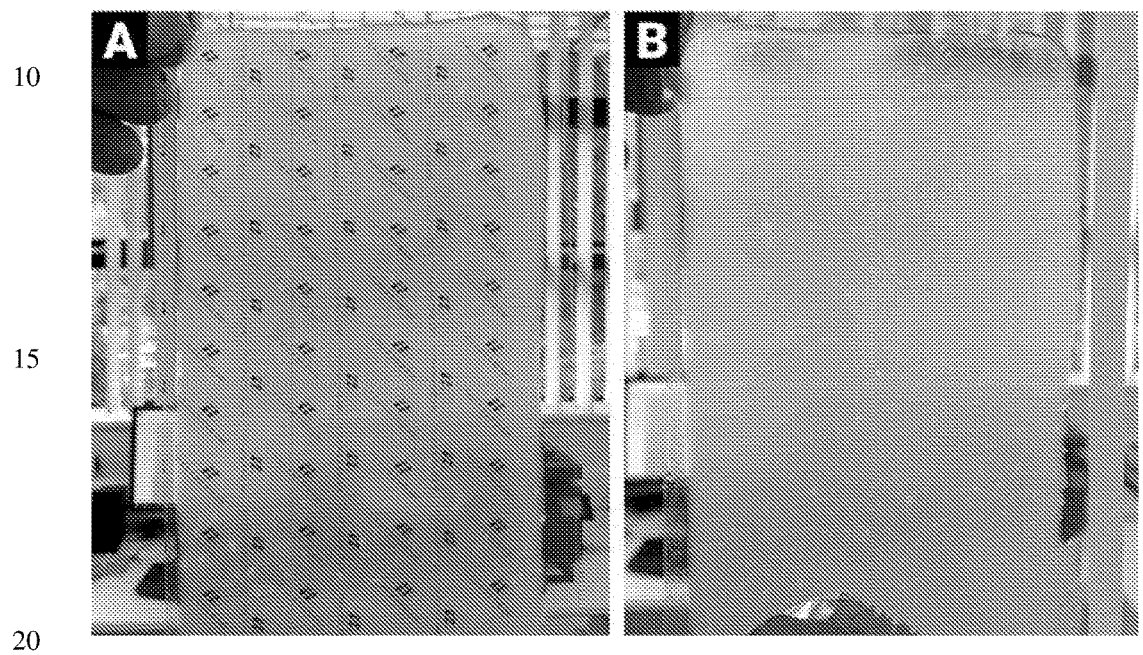
FIG. 2 shows the Fenbufen (A) and prilocaine (B) 5% w/w patches.

It is noted that fenbufen and prilocaine are uniformly distributed in the patch in a form of micro particles, and can potentially be extracted from the patches, despite the incompatibility with compositions and patches of the invention (see FIG. 2.)

Solubility of Drugs for Hormone Therapy

Among tested hormone therapy drugs hydrocortisone showed highest solubility of ~3.5% w/w. Its mass fraction in Medherant patches is higher than in any commercial analogues such as creams (Cortisone® 1% w/w) and ointments (Efcortelan® 2.5% w/w).

Solubility of Other Drugs

All tested anti-infective drugs were able to mix with each grade (A, B and C) of the compositions of the invention. For example, iodine is freely soluble in corresponding gel compositions up to 5% w/w. It should be noted that the fabrication process has limits related to the size of iodine powder. However, achieved concentration of 5% w/w is higher than in products already available on the market by factor of 5 (Inadine® patches).

Silver nitrate demonstrated good solubility of 2.5% w/w in the compositions and patches of the invention.

Chlorquinaldol showed good dissolution in compositions and patches of the invention. Its concentration in patches can be increased up to 15% w/w without any adverse issues. The concentration can further be increased and represents a substantially improvement over existing commercial analogues (1% w/w Nerisone C® cream).

Figure 3:
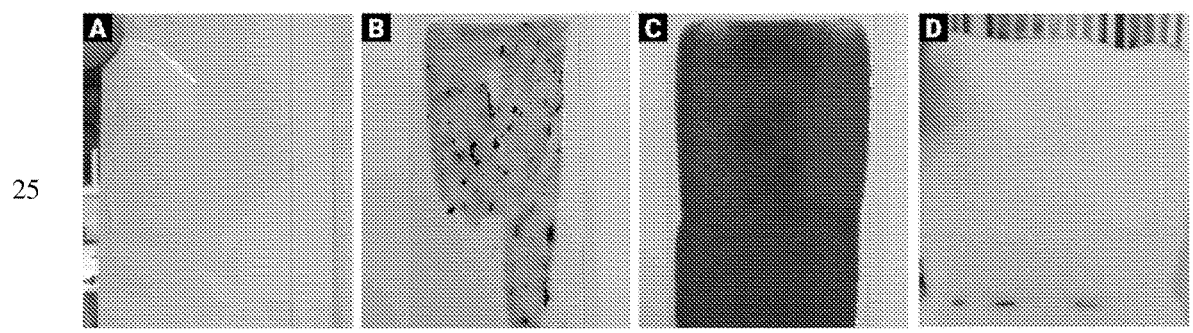
FIG. 3 shows the Medherant patches loaded with anti-infective compounds. Chlorquinaldol (A), iodine (B), silver nitrate (C) and chlorhexidine (D).

Chlorhexidine was found to be soluble in compositions and patches of the invention up to ~3.5% w/w. Despite limited solubility of chlorhexidine, the fabricated patches still contain a higher concentration of the drug in comparison to those existing patches available on the market (Eczmol® 1% w/w, Savlon® 0.1% w/w). Patches containing antiinfective drugs are shown on FIG. 3.

Figure 4:
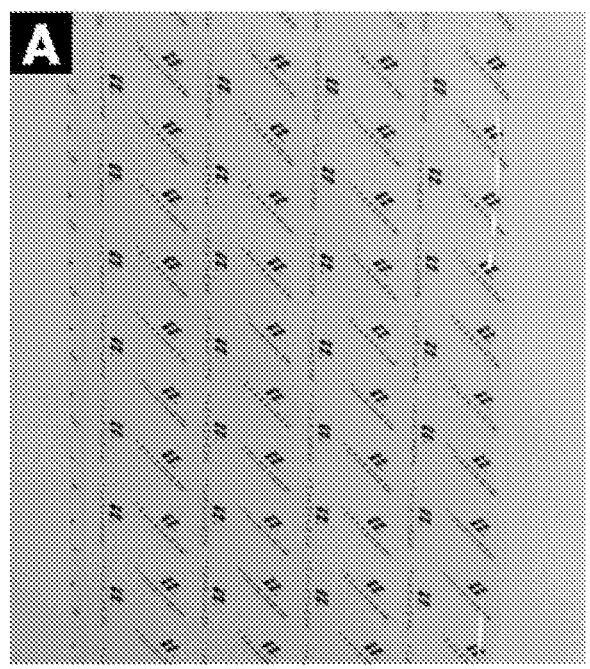
FIG. 4 shows the Medherant nicotine patch 5% w/w.

Nicotine was found to be freely soluble in all grades of the compositions and patches of the invention (see FIG. 4). All 5% w/w patches that were produced contained approximately 71 mg of nicotine on area of 21 cm$^2$. This is a substantial improvement over existing patch systems available on the market which have only 25 mg on a comparable area. If required, the mass fraction of nicotine in Medherant patches can be increased up to 30% w/w.

Obtained solubility data for all tested drugs is summarised in Table 5. We found that 14 out of 19 tested compounds are soluble in compositions and patches of the invention.

TABLE 5

List of drugs used solubility experiments

| No | Drug | Type | Soluble in A | Max. mass fraction, % | Sol. type |
|---|---|---|---|---|---|
| 1 | Ibuprofen | Analgesic | ✓ | 30 | Molecular |
| 2 | Methyl salicylate | | ✓ | 30 | Molecular |
| 3 | Diclofenac epolamine | | ✓ | 5 | Molecular |
| 4 | Levomenthol | | ✓ | 30 | Molecular |
| 5 | Salicylic acid | | ✓ | 30 | Molecular |
| 6 | Ketoprofen | | ✓ | 30 | Molecular |
| 7 | Fenbufen | | x | — | Dispersion |
| 8 | Prilocaine | | x | — | Dispersion |
| 9 | Lidocaine | | ✓ | 30 | Molecular |
| 10 | Piroxicam | | ✓ | 2.5 | Molecular |
| 11 | Flurbiprofen | | ✓ | 15 | Molecular |
| 12 | Salsalate | | ✓ | 10 | Molecular |
| 13 | Indomethacin | | ✓ | 10 | Molecular |
| 14 | Aspirin | | x | — | Dispersion |
| 15 | Paracetamol | | x | — | Dispersion |
| 16 | Naproxen | | x | — | Dispersion |
| 17 | Prednisolone | Hormone | x | — | Dispersion |
| 18 | Hydrocortisone | therapy | ✓ | 3.5 | Molecular |
| 19 | p-Estradiol | | ✓ | 5 | Molecular |
| 20 | Testosterone | | ✓ | 5 | Molecular |
| 21 | Progesterone | | ✓ | 15 | Molecular |
| 22 | Chlorhexidine | Anti- | ✓ | 3.5 | Molecular |
| 23 | Iodine | infective/ | ✓ | 5 | Molecular |
| 24 | Silver nitrate | parasitic/ | ✓ | 2.5 | Molecular |
| 25 | Chlorquinaldol | fungal/ | ✓ | 15 | Molecular |
| 26 | Tetracycline | biotic | ✓ | 3.5 | Molecular |
| 27 | Ivermectin | | ✓ | 5 | Molecular |
| 28 | Nystatin | | ✓ | | Molecular |
| 29 | Praziquantel | | ✓ | 10 | Molecular |
| 30 | Amoxicillin | | x | — | Dispersion |
| 31 | Penicillin G | | x | — | Dispersion |
| 32 | Trimethoprim | | x | — | Dispersion |
| 33 | Artesunate | Anti- | ✓ | 6 | Molecular |
| 34 | Artemisinin | malaria | ✓ | 9 | Molecular |
| 35 | Nicotine | Other | ✓ | 30 | Molecular |
| 36 | Cyclosporine | | ✓ | 5 | Molecular |
| 37 | Methotrexate | | ✓ | 7 | Molecular |
| 38 | Salbutamol | | ✓ | 5 | Molecular |
| 39 | Caffeine | | x | — | Dispersion |
| 40 | Pramipexole | | x | — | Dispersion |

Typical Nicotine Patch Preparation Process

Table List of components used for the synthesis of the nicotine patch

| Scale, g 100 g$^{-1}$ | Item No | Ingredients | Mass fraction, wt % |
|---|---|---|---|
| 73.0 | 1 | Adhesive | 73.0 |
| 25.0 | 2 | Nicotine | 25.0 |
| 2.00 | 3 | Benzyl alcohol | 2.00 |

Preheat Item 1 to 75° C., charge Item 1 into a vessel under nitrogen blanket, subsequently add Items 2 and 3 one by one and heat vessel contents to 75° C. Homogenise at 300 rpm using an overhead stirrer and impeller for a viscous medium for 10 min. Cast the resulting mixture on a release liner and uniformly spread employing a casting instrument. Cure the film in an oven at 90° C. in 50% relative humid atmosphere for 20 min. Apply a backing layer onto the surface upon completion of the curing.

Nicotine Permeation Analysis (Strat-M Membranes):

| | Total permeated amount, ˆg cm−2 | | Flux, ˆg cm−2 | |
|---|---|---|---|---|
| Sample, h | Medherant | Niquitin | Medherant | Niquitin |
| 1 | 363.7 | 116.2 | 363.73 | 116.16 |
| 2 | 469.6 | 205.3 | 152.93 | 112.95 |
| 4 | 588.0 | 366.6 | 59.22 | 80.63 |
| 6 | 703.4 | 496.1 | 57.72 | 64.74 |
| 8 | 817.2 | 618.2 | 56.89 | 61.08 |
| 10 | 929.7 | 729.0 | 56.23 | 55.40 |
| 12 | 1041.8 | 840.7 | 56.07 | 55.84 |

Adhesive Grades Used: F15, F16 and F17

| | Adhesive | | |
|---|---|---|---|
| Properties | F15 | F16 | F17 |
| Viscosity at 100° C., mPa S | 1580 | 2010 | 1890 |
| Skinning time/seconds | >900 | 222 | 631 |

Drugs Tested: Ibuprofen, Lidocaine, Methyl Salicylate

| Properties/Adhesive | Ibuprofen | Lidocaine | Methyl salicylate |
|---|---|---|---|
| Melting point, ° C. | 75-77 | 68 | −8.6 |
| LogP | 3.97 | 2.26 | 2.55 |
| Molecular structure | 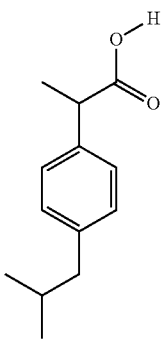 | 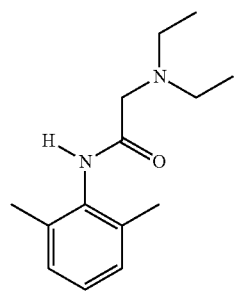 [SMILES: CCN(CC)CC(=O)Nc1c(C)cccc1C] | 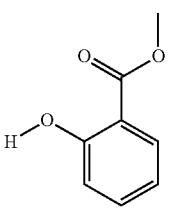 |

Solubility:

|  | Adhesive | | |
| --- | --- | --- | --- |
| API | F15 | F16 | F17 |
| Ibuprofen | ✓ | ✓ | ✓ |
| Lidocaine | ✓ | ✓ | ✓ |
| Methyl salicylate | ✓ | ✓ | ✓ |

Skinning time test aim to measure the time needed to create a cured skin on top of a hot adhesive sample. Test is done in a ventilated room at 23° C. with 50% relative humidity. A heated plate is set at 120° C. 5 grams of adhesive is put in an aluminium flat-bed round-shaped 6-cm-diameter tray, and put on the heated plate when the chronometer is started. Every 5 seconds, the cleaned point of a metallic tool (tip of knife blade, screw, paper clip) is put in contact with the surface of adhesive. When removing the point from the surface, it creates a stretching string of soft adhesive. The skinning time is read onto the chronometer when there is no such string, as the surface of the adhesive is hardening and is only slightly deformed by the point of the tool. This operation is repeated several times, each time with a new sample of the same adhesive material, until the standard deviation of the measurement will be under 20 seconds. The average value of skinning time is then reported.

The invention claimed is:

1. A composition for drug delivery to a skin comprising:
    a silyl-containing polymer and at least one drug for drug delivery to the skin;
    wherein the silyl-containing polymer is cross-linked;
    wherein the silyl-containing polymer is one or more polyurethane-polyether, and
    wherein the silyl-containing polymer has a structure as follows:

wherein:
    $R^1$ represents a hydrocarbon-based group;
    $R^2$ represents an aliphatic or aromatic polyether;
    $R^3$ represents a hydrocarbon-based group that comprises 1 to 3 carbon atoms;
    $R^4$ and $R^5$ are each independently selected from a linear or branched alkyl group
    n is an integer greater than or equal to 0; and
    p is an integer equal to 0, 1 or 2;
    wherein n is selected such that the number-average molecular weight of the polymer of formula (I) is greater than 700 Da.

2. The composition according to claim 1, wherein the silyl-containing polymer has two or more silyl groups.

3. The composition according to claim 1, wherein the silyl-containing polymer further comprises a least one group adapted to dissolve or disperse the at least one drug for drug delivery to the skin.

4. The composition according to claim 1, wherein the silyl-containing polymer comprises one or more co-polymers selected form a group consisting of block copolymers, random copolymers, alternating copolymers, and graft copolymers.

5. The composition for drug delivery to the skin comprising:
    a first component obtainable by reacting the silyl-containing polymer according to claim 1 in the presence of a catalyst; and a second component comprising a drug for drug delivery to the skin.

6. The composition according to claim 1, wherein the drug delivery to the skin is transdermal drug delivery.

7. The composition according to claim 1, wherein the silyl-containing polymer has a weight average molecular weight in the range 700 Da to 250 kDa.

8. The composition according to claim 1, further comprising a tackifying resin.

9. The composition according to claim 8, wherein the tackifying resin is selected from: copolymers comprising at least (meth)acrylic monomers and hydrocarbon monomers; and
    polymers containing at least one (meth)acrylic function or chain part, and hydrocarbon chain parts.

10. The composition according to claim 8, wherein the tackifying resin is selected from phenol modified terpene resins, hydrocarbon resins, rosin ester resins, acrylic resins and mixtures thereof.

11. The composition according to claim 8, wherein the tackifying resin has a softening point less than or equal to 150° C.

12. The composition according to claim 8, wherein the tackifying resin is selected from:
    a mixture of styrene-acrylic resins and rosin ester resins; and a dicyclopentadiene-acrylic polymer.

13. The composition according to claim 8, the composition comprising: a) from 20 to 85% by weight of the silyl-containing polymer; and b) from 15 to 80% by weight of the tackifying resin.

14. The composition according to claim 1, further comprising from 0.01 to 3% by weight of at least one catalyst.

15. The composition according to claim 1, wherein the drug has a molecular weight greater than 100 Da.

16. The composition according to claim 1, wherein the drug is for transdermal drug delivery.

17. The composition according to claim 1, wherein the drug is hydrophilic or amphoteric.

18. The composition according to claim 1, wherein the drug is hydrophilic.

19. The composition according to claim 1, wherein the drug is one or more selected from a group consisting of: small molecular drugs, proteins, peptides, enzymes, DNA, RNA, siRNA, antibodies or fragments thereof, vitamins, and minerals.

20. The composition according to claim 1, wherein the drug is selected from the group consisting of: analgesics, anti-inflammatory drugs, hormones, anti-addiction drugs, anti-hypotension drugs, anti-depressants, anti-Alzheimer's drugs, anti-infective, anti-scarring drugs, anti-psychotics, metabolic modulators, pigmentation, nutrients, minerals and vitamins.

21. The composition according to claim 20, wherein the drug is an analgesic.

22. The composition according to claim 21, wherein the analgesic is selected from the group consisting of: isobutylphenylpropanoic acid, capsaicin, isobutylphenylpropanoic acid, flurbiprofen, methyl salicylate, diclofenac epolamine, levomenthol, salicylic acid, ketoprofen, fenbufen, prilocaine, lidocaine, piroxiam, sufentanil, trolamine, or combinations thereof.

23. The composition according to claim 20, wherein the drug is a hormone.

24. The composition according to claim 23, wherein the hormone is selected from: buprenorphine, clobetasone butyrate, clonidine, dexamethasone, diflucortalone valerate, estradiol, estrogen, ethinylestradiol, gestodene, hydrocortisone, levonorgestrel, norelgestromin, norethisterone, prednisolone, teriparatide, testosterone, triamcinolone, or combinations thereof.

25. The composition according to claim 20, wherein the drug is an anti-addiction drug.

26. The composition according to claim 25, wherein the drug is nicotine.

27. A drug delivery patch comprising the composition of claim 1.

28. The drug delivery patch according to claim 27, wherein the patch is a transdermal drug delivery patch.

29. A method, comprising:
   delivering a drug to skin using a composition comprising a silyl-containing polymer and at least one drug for drug delivery to the skin;
wherein the silyl-containing polymer is cross-linked; and
wherein the silyl-containing polymer is one or more polyurethane-polyether, and
wherein the silyl-containing polymer has a structure as follows:

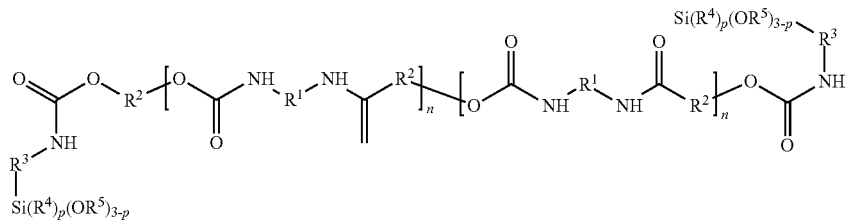

wherein:
   $R^1$ represents a hydrocarbon-based group;
   $R^2$ represents an aliphatic or aromatic polyether;
   $R^3$ represents a hydrocarbon-based group that comprises 1 to 3 carbon atoms;
   $R^4$ and $R^5$ are each independently selected from a linear or branched alkyl group
   n is an integer greater than or equal to 0; and
   p is an integer equal to 0, 1 or 2;
   wherein n is selected such that the number-average molecular weight of the polymer of formula (I) is greater than 700 Da.

30. The method of claim 29, wherein the composition further comprises a tackifying resin.

31. The method of claim 30, wherein the composition comprises:
   a) from 20 to 85% by weight of the silyl-containing polymer; and
   b) from 15 to 80% by weight of the tackifying resin.

32. The method of claim 29, wherein the composition further comprises from 0.01 to 3% by weight of at least one catalyst.

33. The composition according to claim 20, wherein the drug is buprenorphine or clonidine.

* * * * *